US006462016B1

(12) United States Patent
Wakita et al.

(10) Patent No.: US 6,462,016 B1
(45) Date of Patent: *Oct. 8, 2002

(54) METHOD FOR SCREENING AGONIST OR ANTAGONIST OF THE MAXADILAN RECEPTOR PARTICIPATING IN VASODILATING ACTION, AND COMPOUND FOUND BY THE METHOD

(75) Inventors: Kawori Wakita, Yokohama (JP); Osamu Moro, Lexington, MA (US); Manami Ohnuma, Kamakura (JP); Ethan A. Lerner, Newton, MA (US); Masahiro Tajima, Yokohama (JP)

(73) Assignees: Shiseido Company, Ltd., Tokyo (JP); The General Hospital Corporation, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/969,744

(22) Filed: Nov. 13, 1997

Related U.S. Application Data

(62) Division of application No. 08/540,033, filed on Oct. 6, 1995, now abandoned.

(51) Int. Cl.$^7$ .......................... A61K 38/16; C07K 14/00
(52) U.S. Cl. .............................. 514/2; 514/12; 514/830; 514/870; 514/886; 514/906; 514/929; 530/324; 530/307
(58) Field of Search ................................. 530/300, 324, 530/307; 514/2, 12, 830, 870, 886, 906, 929

(56) References Cited

U.S. PATENT DOCUMENTS

| 5,480,864 A | * | 1/1996 | Tajima et al. | 514/2 |
| 5,637,309 A | * | 6/1997 | Tajima et al. | 424/423 |
| 5,763,271 A | * | 6/1998 | Ribeiro et al. | 435/325 |

FOREIGN PATENT DOCUMENTS

| WO | 91/00293 | 1/1991 |
| WO | 95/04829 | 2/1995 |

OTHER PUBLICATIONS

Grevelink et al, J. Pharmacol Exp. Ther, 1995, 216: 234–41.*
Bylund & Yamamura, Methods in Neurotransmitter Receptor Analysis, H.I. Yamanura, Ed, Raven Press, NY, 1990 p. 1–4.*
Entzeroth et al., Lite Sciences 56:PL 19–25.*
Lerner et al (J. Invest. Pernatol, 100, (4) 593, 1993).*
Lerner et al., "Cloning and Functional Expression of the Gene Encoding this Potent Vasodilator Peptide", The Journal of Biological Chemistry, vol. 267, No. 2, pp. 1062–1066, Jan. 15, 1992.
Ribeiro et al., A Novel Vasodilatory Peptide from the Salivary Glands of the Sand Fly *Lutzomyia longipalpis*, Science, vol. 24, pp. 212–214, 1987.
Smith et al., "Single–Step Purification of Polypeptides Expressed in *Escherichia coli* as Fusions with Glutathione S–transferase", Gene, 67, pp. 31–40, 1988.
Tortora and Anagnostakos, Principles of anatomy and Physiology, 1984, p. 311.*
Parkinson et al, General Pharmacology, 1994, vol. 25, pp. 1053–1058. Abstract only.*
Chang et al, Neuron, 1993, vol. 11, pp. 1187–1195.Abstract only.*
Carey, Journal of the American society of Nephrology, 1992, vol. 2, pp. 1265–1270. Abstract only.*
Cox et al, Journal of Physiology, 1978, vol. 282, pp. 471–483. Abstract only.*
Phillips et al, Endocrinology, 1990, vol. 126, pp. 1478–1484. Abstract only.*
Nishimura et al, Med J Kinki Univ., 1992, vol. 17, pp. 21–24. Abstract only.*
Burgess et al (J. Cell Bio., 111:2129–2138), 1990.*
Lazar et al (Mol. and Cell. Biol., 8:1247–1252), 1988.*
Tao et al (J. Immunol., 143:2595–2601), 1989.*
Bowie et al (Sciece, 257:1306–1310), 1990.*
Zhu et al (BBRC, 177:771–776), 1990.*

* cited by examiner

Primary Examiner—Anthony C. Caputa
Assistant Examiner—Karen A. Canella
(74) Attorney, Agent, or Firm—Wenderoth, Lind & Ponack, L.L.P.

(57) ABSTRACT

There are provided a method to screen agonist or antagonist of the maxadilan receptor participating in vasodilating action, wherein a receptor of maxadilan is used, compounds which specifically bind to the receptor, and a tissue preparation having the receptor. The compounds are variants of maxadilan from the salivary glands of the sand fly.

20 Claims, 15 Drawing Sheets

```
      1         5          10         15         20         25         30         35         40         45         50         55         60
      |         |          |          |          |          |          |          |          |          |          |          |          |
Max   GSIL-CDATCQFRKAIDDCQKQAHHSNVLQTSVQTTATFTSMDTSQLPGNSVFKECMKQKKKEFKAGK
M42   GS-SDATCQFRKAIDDCQKQAHHSNVLQTSVQTTATFTSMDTSQLPGNSVFKECMKQKKKEFKAGK
M45   GS-CDATSQFRKAIDDCQKQAHHSNVLQTSVQTTATFTSMDTSQLPGNSVFKECMKQKKKEFKAGK
M44B  GS-SDATSQFRKAIDDCQKQAHHSNVLQTSVQTTATFTSMDTSQLPGNSVFKECMKQKKKEFKAGK
NSP   GSG-----QFRKAIDDCQKQAHHSNVLQTSVQTTATFTSMDTSQLPGNSVFKECMKQKKKEFKAGK
M46   GS-CDATCQFRKAIDDSQKQAHHSNVLQTSVQTTATFTSMDTSQLPGNSVFKECMKQKKKEFKAGK
M48B  GS-CDATCQFRKAIDDCQKQAHHSNVLQTSVQTTATFTSMDTSQLPGNSVFKEAMKQKKKEFKAGK
M98   GS-CDATCQFRKAIDDCQKQAHHSNV--------RTSMDTSQLPGNSVFKEAMKQKKKEFKAGK
M65   GS-CDATCQFRKAIDDCQKQAHHSNV--------RTSMDTSQLPGNSVFKECMKQKKKEFKAGK
M67   GS-CDATCQ-----------------------------------PGNSVFKECMKQKKKEFKAGK
M64   GS-CDATCQ-----------------------------------NSVFKECMKQKKKEFKAGK
```

FIG. I

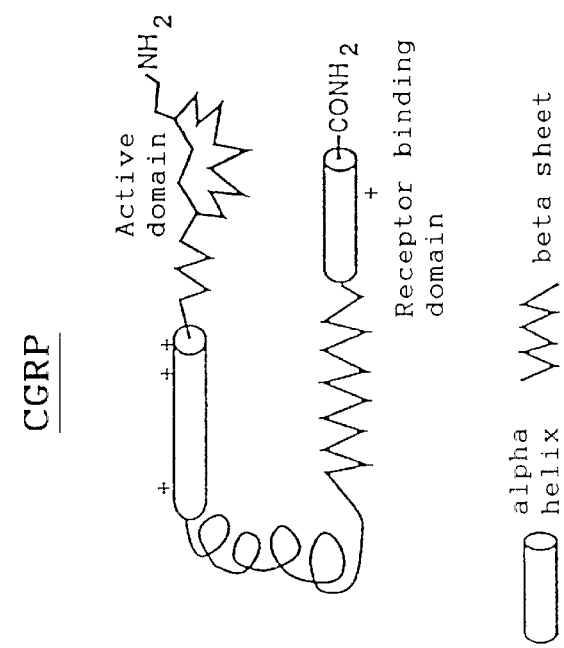
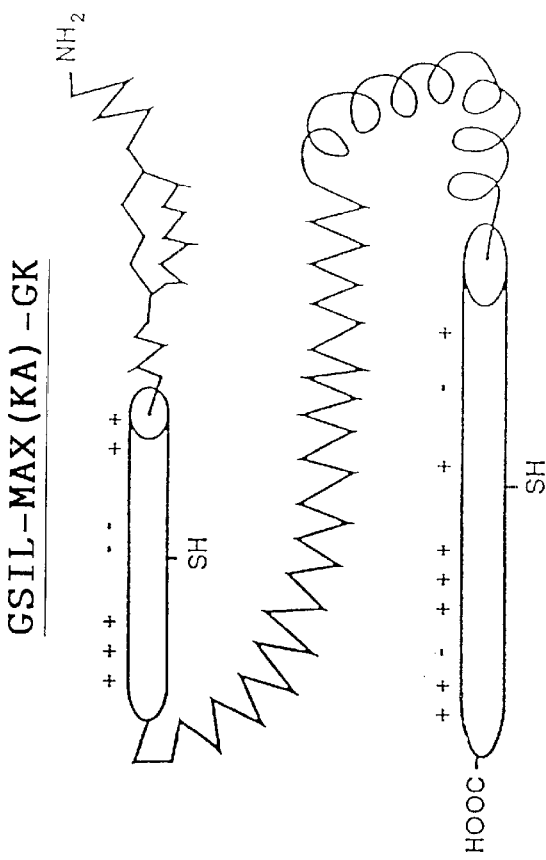
FIG. 12

FIG. 14
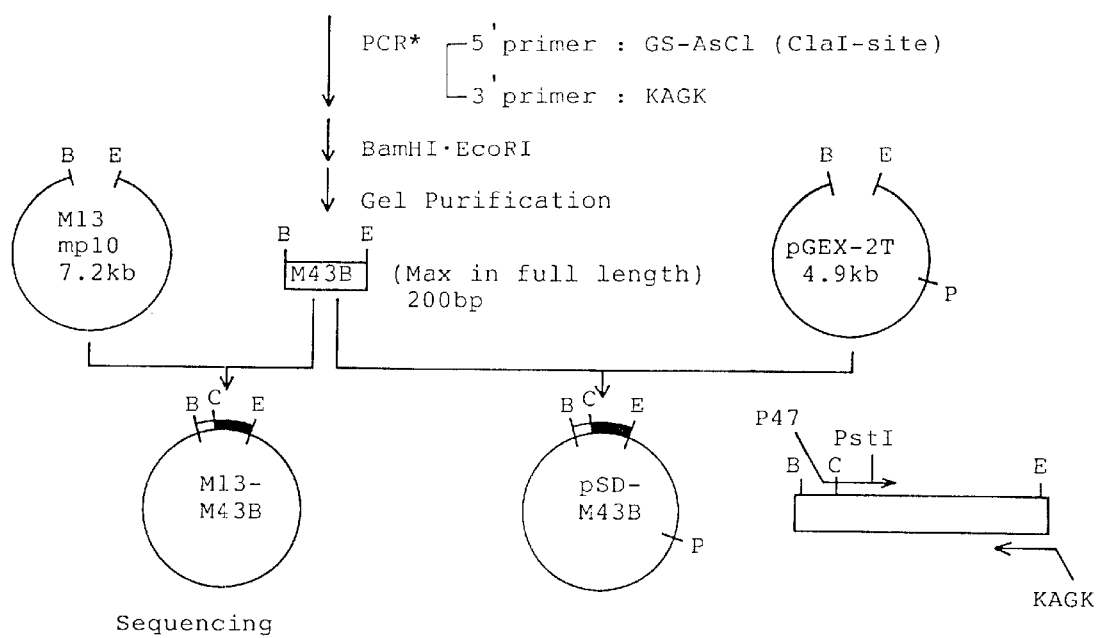
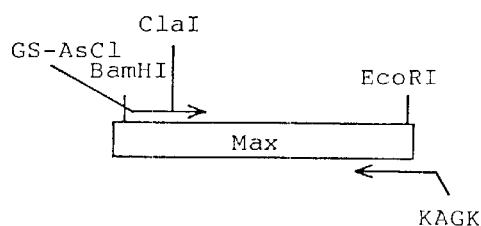

Step 3)
FIG. 15
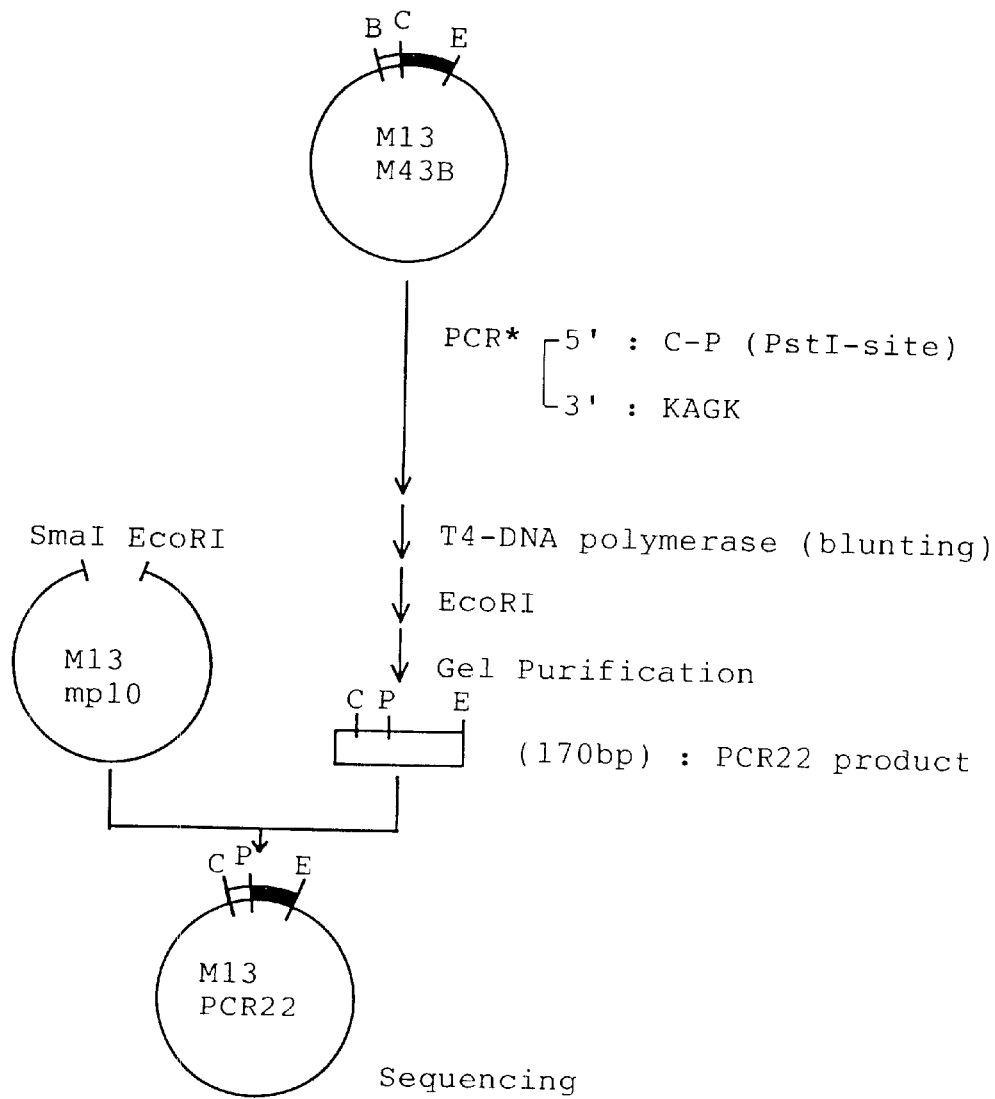
*PCR
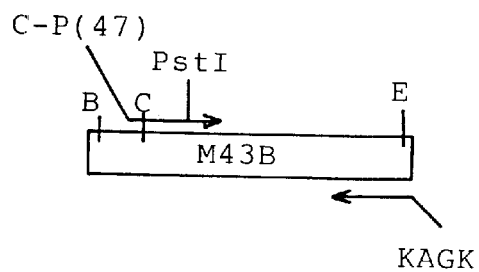

step 4)

FIG. 19
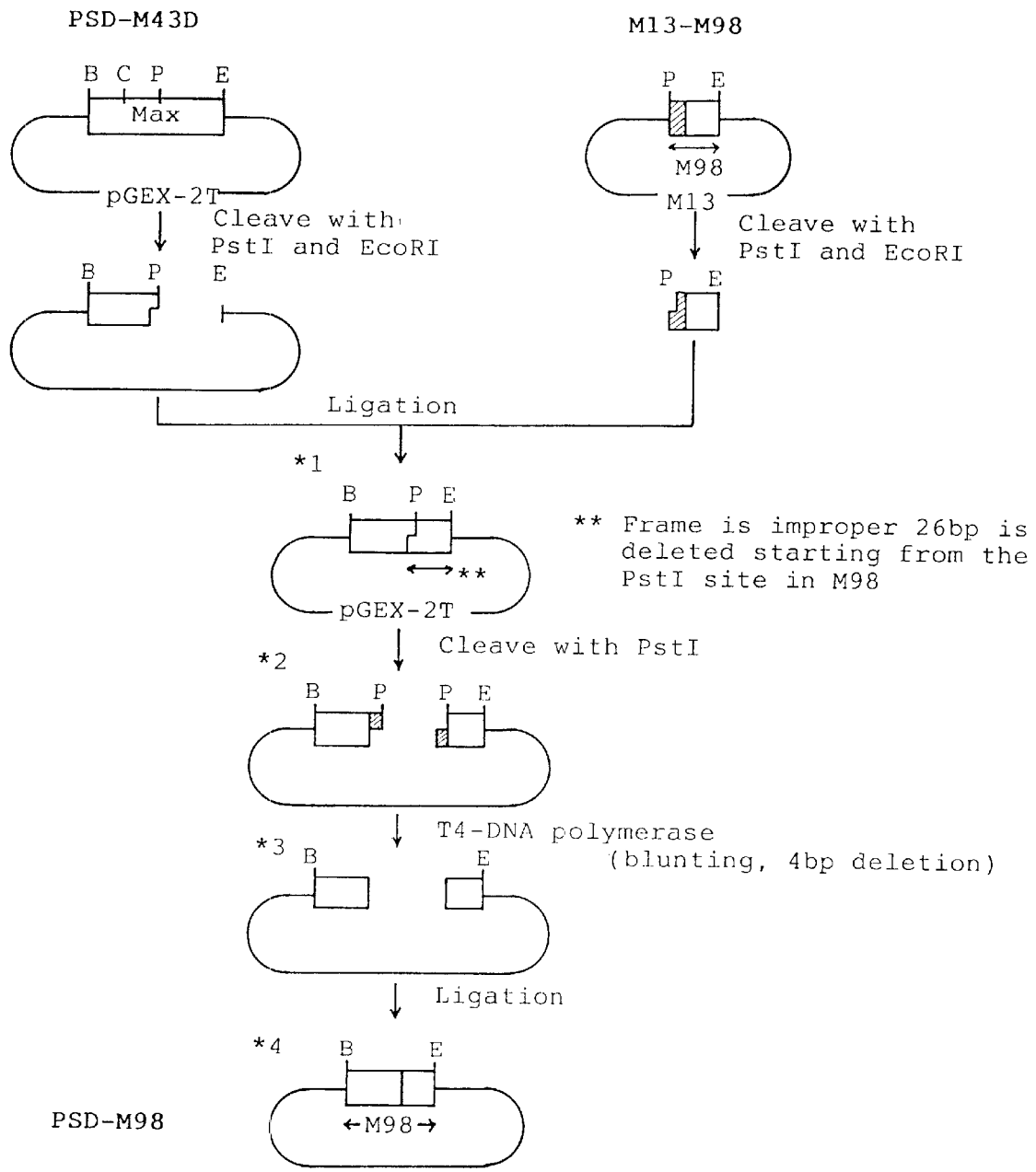
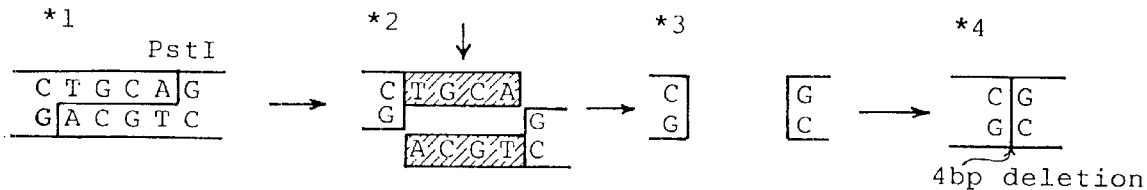

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 61 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Cys Asp Ala Thr Cys Gln Phe Arg Lys Ala Ile Asp Asp Cys Gln Lys
1              5                    10                 15

Gln Ala His His Ser Asn Val Leu Gln Thr Ser Val Gln Thr Thr Ala
            20                  25                  30

Thr Phe Thr Ser Met Asp Thr Ser Gln Leu Pro Gly Asn Ser Val Phe
            35                  40                  45

Lys Glu Cys Met Lys Gln Lys Lys Glu Phe Lys Ala
 50                  55                  60

(2) INFORMATION FOR SEQ ID NO:2:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Gly Ser Ile Leu Cys Asp Ala Thr Cys Gln Phe Arg Lys Ala Ile Asp
 1               5                  10                  15

Asp Cys Gln Lys Gln Ala His His Ser Asn Val Leu Gln Thr Ser Val
            20                  25                  30

Gln Thr Thr Ala Thr Phe Thr Ser Met Asp Thr Ser Gln Leu Pro Gly
            35                  40                  45

Asn Ser Val Phe Lys Glu Cys Met Lys Gln Lys Lys Glu Phe Lys
 50                  55                  60

Ala Gly Lys
 65

(2) INFORMATION FOR SEQ ID NO:3:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Gly Ser Ser Asp Ala Thr Cys Gln Phe Arg Lys Ala Ile Asp Asp Cys
 1               5                  10                  15

Gln Lys Gln Ala His His Ser Asn Val Leu Gln Thr Ser Val Gln Thr
            20                  25                  30

Thr Ala Thr Phe Thr Ser Met Asp Thr Ser Gln Leu Pro Gly Asn Ser
            35                  40                  45

Val Phe Lys Glu Cys Met Lys Gln Lys Lys Glu Phe Lys Ala Gly
 50                  55                  60

Lys
 65

(2) INFORMATION FOR SEQ ID NO:4:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

-continued

```
Gly Ser Cys Asp Ala Thr Ser Gln Phe Arg Lys Ala Ile Asp Asp Cys
 1               5                  10                  15

Gln Lys Gln Ala His His Ser Asn Val Leu Gln Thr Ser Val Gln Thr
                20                  25                  30

Thr Ala Thr Phe Thr Ser Met Asp Thr Ser Gln Leu Pro Gly Asn Ser
            35                  40                  45

Val Phe Lys Glu Cys Met Lys Gln Lys Lys Glu Phe Lys Ala Gly
     50                  55                  60

Lys
65
```

(2) INFORMATION FOR SEQ ID NO:5:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Gly Ser Ser Asp Ala Thr Ser Gln Phe Arg Lys Ala Ile Asp Asp Cys
 1               5                  10                  15

Gln Lys Gln Ala His His Ser Asn Val Leu Gln Thr Ser Val Gln Thr
                20                  25                  30

Thr Ala Thr Phe Thr Ser Met Asp Thr Ser Gln Leu Pro Gly Asn Ser
            35                  40                  45

Val Phe Lys Glu Cys Met Lys Gln Lys Lys Glu Phe Lys Ala Gly
     50                  55                  60

Lys
65
```

(2) INFORMATION FOR SEQ ID NO:6:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Gly Ser Gly Gln Phe Arg Lys Ala Ile Asp Asp Cys Gln Lys Gln Ala
 1               5                  10                  15

His His Ser Asn Val Leu Gln Thr Ser Val Gln Thr Thr Ala Thr Phe
                20                  25                  30

Thr Ser Met Asp Thr Ser Gln Leu Pro Gly Asn Ser Val Phe Lys Glu
            35                  40                  45

Cys Met Lys Gln Lys Lys Lys Glu Phe Lys Ala Gly Lys
     50                  55                  60
```

(2) INFORMATION FOR SEQ ID NO:7:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Gly Ser Cys Asp Ala Thr Ser Gln Phe Arg Lys Ala Ile Asp Asp Ser
1               5                   10                  15

Gln Lys Gln Ala His His Ser Asn Val Leu Gln Thr Ser Val Gln Thr
                20                  25                  30

Thr Ala Thr Phe Thr Ser Met Asp Thr Ser Gln Leu Pro Gly Asn Ser
            35                  40                  45

Val Phe Lys Glu Ala Met Lys Gln Lys Lys Glu Phe Lys Ala Gly
    50                  55                  60

Lys
65

(2) INFORMATION FOR SEQ ID NO:8:

(i) SEQUENCE CHARACTERISTICS:
        (A) LENGTH: 65 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Gly Ser Cys Asp Ala Thr Cys Gln Phe Arg Lys Ala Ile Asp Asp Cys
1               5                   10                  15

Gln Lys Gln Ala His His Ser Asn Val Leu Gln Thr Ser Val Gln Thr
                20                  25                  30

Thr Ala Thr Phe Thr Ser Met Asp Thr Ser Gln Leu Pro Gly Asn Ser
            35                  40                  45

Val Phe Lys Glu Ala Met Lys Gln Lys Lys Glu Phe Lys Ala Gly
    50                  55                  60

Lys
65

(2) INFORMATION FOR SEQ ID NO:9:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Gly Ser Cys Asp Ala Thr Cys Gln Phe Arg Lys Ala Ile Asp Asp Cys
1               5                   10                  15

Gln Lys Gln Ala His His Ser Asn Val Arg Thr Ser Met Asp Thr Ser
                20                  25                  30

Gln Leu Pro Gly Asn Ser Val Phe Lys Glu Cys Met Lys Gln Lys Lys
            35                  40                  45

Lys Glu Phe Lys Ala Gly Lys
    50                  55

(2) INFORMATION FOR SEQ ID NO:10:

(i) SEQUENCE CHARACTERISTICS:
        (A) LENGTH: 46 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:10:

```
Gly Ser Cys Asp Ala Thr Cys Gln Phe Arg Lys Ala Ile Asp Asp Cys
1               5                   10                  15
Gln Lys Gln Ala His His Ser Asn Val Pro Gly Asn Ser Val Phe Lys
            20                  25                  30
Glu Cys Met Lys Gln Lys Lys Lys Glu Phe Lys Ala Gly Lys
        35                  40                  45
```

(2) INFORMATION FOR SEQ ID NO:11:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Gly Ser Cys Asp Ala Thr Cys Gln Asn Ser Val Phe Lys Glu Cys Met
1               5                   10                  15
Lys Gln Lys Lys Lys Glu Phe Lys Ala Gly Lys
            20                  25
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Gly Ser Cys Asp Ala Thr Cys Gln
1               5
```

(2) INFORMATION FOR SEQ ID NO:13:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

```
CCGGATCCTG TGATGCAACA TGCCAATTTC GAAAGGCCAT CGATG          45
```

(2) INFORMATION FOR SEQ ID NO:14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

```
GGGAATTCAC TTGCCGGCTT TAAATTCC                             28
```

(2) INFORMATION FOR SEQ ID NO:15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:15:

```
CCATCGATGA CTGCCAGAAG CAGGCGCATC ATAGCAATGT TCTGCAG                    47
```

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Gly Ser Ile Leu
  1
```

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:17:

```
CCGGATCCGG                                                             10
```

METHOD FOR SCREENING AGONIST OR ANTAGONIST OF THE MAXADILAN RECEPTOR PARTICIPATING IN VASODILATING ACTION, AND COMPOUND FOUND BY THE METHOD

This application is a divisional application of now abandoned application Ser. No. 08/540,033, filed Oct. 6, 1995.

BACKGROUND OF THE INVENTION

1. Field of the Invention

The present invention relates to a method for screening for an agonist or antagonist participating in vasodilating action, and compounds obtained by the method. More specifically, the invention relates to a method for screening for an agonist or antagonist using a receptor of maxadilan, and a compound which specifically binds to the receptor, and further, according to circumstances, promotes the cAMP production of a culture cell having a certain cAMP production ability.

2. Description of the Related

Maxadilan is known to exist i n the sialaden of the sand fly *Lutzomyia longipalpis* which is a sucking insect. When applied on the epidermis of animals, maxadilan causes erythema without itch and pain, and is considered to be a strong vasodilator. This biological action is known to be very analogous to the action of calcitonin gene-related peptide (CGRP).

Purification of maxadilan from the salivary glands of the sand fly; the nucleotide sequence encoding its amino acid sequence; and cloning of the gene comprising the nucleotide sequence; and expression of the recombinant maxadilan are announced, for example, in WO 91/00293 and E. A. Lerner et al., J. Bio. Chem. 267, 1062–1066 (1992). Lerner et al. cloned a DNA encoding a fused protein of the recombinant maxadilan with glutathione S-transferase (GST); expressed the fused protein; and cleaved the fused protein with factor Xa; and thereby obtained the recombinant maxadilan as a product in which a peptide fragment (GIL–) consisting of three amino acid residues binds to the N-terminal cysteine of maxadilan (the first cysteine of natural maxadilan; namely corresponding to Cys (1) of SEQ ID NO: 1 of the sequence listing).

Further, the present inventors have already found that a recombinant (see SEQ ID NO: 2) in which a peptide fragment (GSIL–) binds to the N-terminal cysteine of natural maxadilan has an erythema formation activity superior to that of natural maxadilan. In the present specification, maxadilan merely referred to means the recombinant represented by SEQ ID NO: 2.

These recombinant maxadilans are common to CGRP in the point of showing a strong erythema formation activity (hereafter merely referred to as "erythema activity"), but draws attention in the point that they show an erythema activity of almost 500-times that of CGRP per one molecule, and the effect lasts for a longer period of time. Therefore, interest in provision of further variants of maxadilan and evaluation results of these physiological activities is neverending.

An in vivo test using as erythema formation activity induced by intracutaneously injecting a test polypeptide into white rabbits has been chiefly used in evaluation for the activity. However, a system which is simple and capable of evaluating activities other than erythema formation activity as well as erythema formation activity, is desired. If such an evaluation system is available, it is believed that it will be easy to conduct evaluation on not only variants of maxadilan but various non-peptide compounds.

Thus, the object of the invention lies in providing an in vitro test method, said method being a method for screening for compounds capable of evaluating activities having correlation with the erythema formation activity and other activities. Further, it is also an object of the invention to provide novel compounds selected by such screening method.

SUMMARY OF THE INVENTION

The present inventors have created various variant maxadilans, and have investigated correlation between these structures and actions. Further, we found that maxadilan specifically binds to specific tissue preparations from mammals, and in certain culture cells, the production amount of cyclic adenosine 3',5'-mono-phosphoric acid (cAMP) is enhanced by maxadilan. Among the above various variant maxadilans, there are those which have the ability to inhibit the binding of maxadilan to the tissue preparation (competitive binding ability), and moreover, enhance cAMP production amount. Thus, it was confirmed that there is a certain correlation between the binding inhibition ability and the cAMP production ability, and the erythema formation ability.

According to the invention, based on such findings, these are provided, for example, as to vasodilating action, according to circumstances, a method for screening for compounds inhibiting such action, and compounds selected by such method.

Thus, the first embodiment of the invention is a method for screening for an agonist or antagonist participating in vasodilating action, said method comprising (A) a step of preparing a tissue preparation derived from a mammal, to which maxadilan specifically binds, (B) a step of preparing an analyte (C) a step of contacting the tissue preparation of the step (A) with the analyte of the step (B), (D) a step of assaying the binding affinity of the analyte to the tissue preparation, in the step (C), (E) when the binding affinity in the step (D) is positive, a further step of assaying the influence of the analyte having such action on the cAMP production ability of an animal culture cell to which maxadilan specifically binds and which has a cAMP production ability, and (F) a step of determining whether the analyte is an agonist or antagonist, based on the results of the step (D) and the step (E)

The second embodiment of the invention is a mammalian preparation having sites (receptors) to which maxadilan specifically binds, the preparation being utilizable for the screening method.

The third embodiment of the invention is a variant maxadilan which specifically binds to a tissue preparation derived from a mammal, having sites to which maxadilan specifically binds, or, according to circumstances, a variant maxadilan which has the above property, and, moreover, promotes the production of cAMP in an animal culture cell which maxadilan specifically binds to and has cAMP production ability.

The thus provided variant maxadilans exhibit binding ability to the receptor of the tissue preparation (ability to competitively inhibit maxadilan), and it is considered that, among them, such a variant maxadilan having, in addition, the cAMP production promotion ability is one acting as an agonist on maxadilan receptors, and such a variant maxadilan exhibiting no cAMP production promotion ability is one acting as an antagonist on maxadilan receptors.

BRIEF DESCRIPTION OF DRAWINGS

FIG. 1 is a list wherein the variant maxadilans provided by the invention are represented based on one-letter symbols of amino acids;

FIG. 12 is a schematic drawing showing the secondary structure of maxadilan based on the formula of Chou & Fasman;

FIG. 14 is a process drawing for construction of a vector M13-M43B;

FIG. 15 is a process drawing for construction of a vector M13PCR22;

FIG. 19 is a process drawing for construction of pSD-M98; and

DETAILED DESCRIPTION OF THE INVENTION

Figure 2:
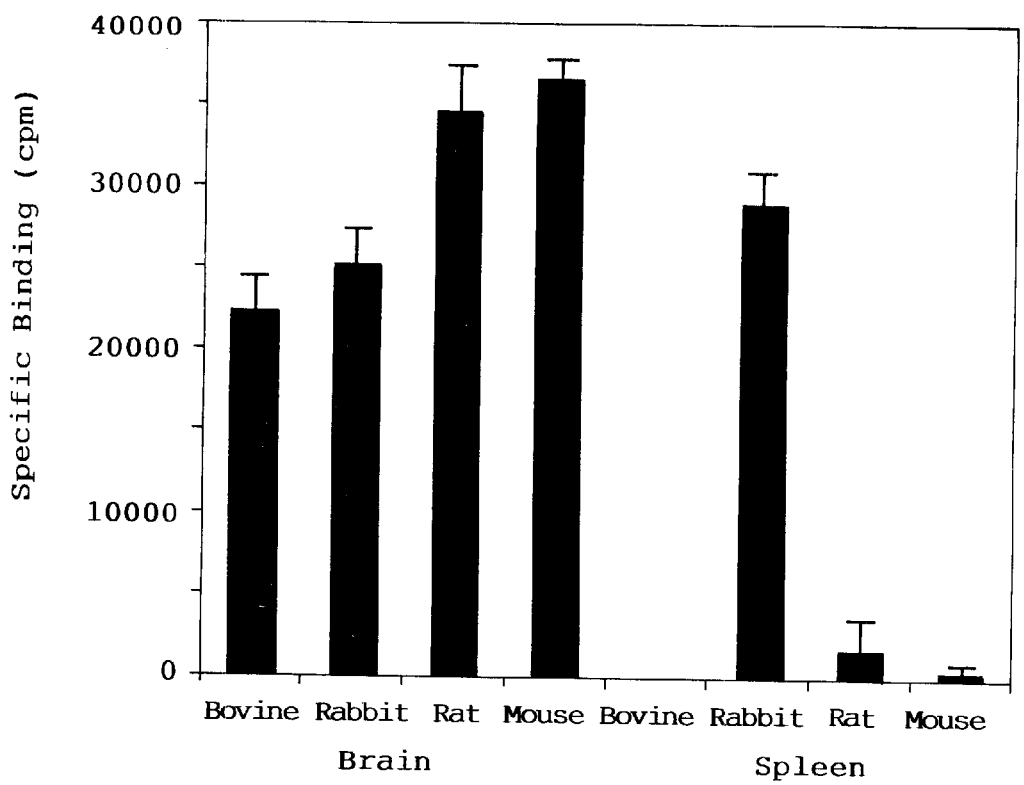
FIG. 2 is a graph showing the binding affinity of maxadilan to the crude membrane fractions from the brains of a bovin, rabbit, rat and mouse, and the crude membrane fractions from their pancreata.

For convenience on description of the invention, expression of α-amino acids in the specification and the attached drawings is based on the following three-letter symbols and one-letter symbols conventional in the concerned technical field.

| Common name | Three-letter symbol | One-letter symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Nucleotides are specified by chemical names of bases, and the following standard abbreviations specifying respective nucleotides are used in the present specification and the attached drawings.

Adenine A

Thymine T

Guanine G

Cytosine C

Uracil U

Figure(s) in the Parenthesis following the three-letter expression of α-amino acids represent(s) the Position number of each amino acid in the amino acid sequence represented by SEQ ID NO: 1.

"Maxadilan specifically binds" means that various peptides including neuropeptides having a vasodilating action, CGRP, vasoactive intestinal polypeptides (VIP), etc., and non-peptide intracerebral signal mediators including carbamylcholine hydrochloride, 3-hydroxytyramine, etc., and so on do not bind, and only maxadilan binds. Therefore, a site to which maxadilan specifically binds can be regarded as a position where a maxadilan-specific receptor (also referred to as "maxadilan receptor") is expressed.

As tissue preparations having such binding sites, there can be mentioned tissue preparations obtained as crude membrane fractions from the brain, pancreas and aorta of a rabit, the brain of a rat, the brain and aorta of a mouse, and the brain of a human being, although it is not intended to be limited there-to Further, specific culture cells such as human neuroblastomas (e.g., NBf1 cell line) and rat adrenal medulla melanocytomas (e.g., PC12 cell line, available from ATCC) are also included in the tissue preparations of the invention.

Contact of such a tissue preparation with an analyte (one of various variant maxadilans or a non-peptide compound) can be conducted by carrying out incubation at temperatures at which denaturation of the tissue preparation is not caused, for example, around 4° C. The binding affinity of the variant maxadilan to the tissue preparation can be determined, for example, by conducting an experiment for investigating competitive binding of the analyte in various concentrations to the tissue preparation in the coexistence of radioactive maxadilan ($^{125}$I-Max), and assaying the degree of the inhibition of binding of $^{125}$I-Max by the analyte. It is, thus, possible to evaluate the binding affinity of the variant maxadilan to the tissue preparation.

Then, an analyte whose above-mentioned binding affinity turned out positive is evaluated for cAMP production ability through a culture test using an animal culture cell which maxadilan specifically binds to and has cAMP production ability. The evaluation of cAMP production ability can be conducted by assaying the cAMP amount in the resultant culture. Although any cell line can be used as the culture cell so long as it satisfies the object of the invention, it is convenient and preferable to use a commercial available rat adrenal medulla melanocytoma (PC-12).

From the assay results of the binding affinity to the tissue preparation and the promotion action of cAMP production in the culture cell, it can be judged whether the analyte variant maxadilan is an agonist or antagonist on the maxadilan receptor, or can not be classified into any of them. Namely, it can be concluded that an analyte having the above binding affinity and the cAMP production promotion action is an agonist of the maxadilan receptor, and an analyte having the above binding affinity but not having the cAMP production promotion action is an antagonist on the maxadilan receptor.

Thus, according to the invention, it becomes possible to provide, for example, pharmaceutical preparations having a regulated vasodilating action, etc., and pharmaceutical preparations inhibiting the information transmission pathway, etc.

As stated above, a cell preparation capable of expressing a maxadilan-specific receptor is provided according to the invention, too.

Further, a compound specifically binding to such receptor is also provided. The compounds of the invention include all compounds including polypeptides so long as they can bind to the receptors.

The invention is described below referring to variant maxadilans, but the invention is not limited thereto.

According to the above screening method of the invention, one selected from the group consisting of a) such a polypeptide that, in the amino acid sequence represented by SEQ ID NO: 1, which is regarded as the fundamental structure part of maxadilan, the polypeptide has the sequence of Gln (6) to Ala (61), and either all or part of the Cys (1) to Cys (5) part is deleted, or at least one of Cys (1) and Cys (5) is replaced by amino acid(s) other than Cys, preferably by Ser, and a derivative of the polypeptide, b) such a polypeptide that, in the amino acid sequence represented by SEQ ID NO: 1, all or part of the Leu (24) to Gly (44) part is deleted, and a derivative of the polypeptide, and such a polypeptide that, in the amino acid sequence represented by SEQ ID NO: 1, at least one of Cys (14) and Cys (51) is replaced by amino acid(s) other than Cys, and a derivative of the polypeptide, specifically binds to the maxadilan receptor. These variant maxadilans exhibit competitive binding affinity with maxadilan on the receptor, and can be confirmed by competitive inhibition of labeled maxadilan.

Among them, variant maxadilans classified into the group a) have also an action to promote cAMP production in the cAMP-producing animal culture cell. They further exhibit a strong erythema formation action when intracutaneously injected into a rabbit, and can be used as an agonist to the maxadilan receptor.

Variant maxadilans classified into the group b) do not promote the cAMP production. Therefore, they can be used as an antagonist to the maxadilan receptor.

The derivative of a polypeptide including the variant maxadilan can be, for example, one having the additional peptide residue remaining in a state of being bound to the N-terminal amino acid residue, when it is intended to produce the polypeptide of the invention as an appropriate fused protein, and process the resultant fused protein to obtain the desired polypeptide. The additional peptide residue is not limited because various ones are included depending on the kind of fused proteins used and the kind of proteases used for processing (cleavage), but as specific examples thereof, there can, for example, be mentioned Gly-Ser-Ile-Leu-(SEQ ID No:16), Gly-Ile-Leu-, Gly-Ser- and Gly-Ser-Gly- when glutathione S-transferase (GST) was used as the fused protein. These peptides can be modified at the functional group of each amino acid residue with an acyl group, an alkyl group or the like.

Likewise, the derivative of the polypeptide can be one having an additional amino acid or peptide residue at the C-terminus of the polypeptide of the invention, or can be one wherein the carboxyl group of the C-terminal amino acid is converted to a carbamoyl group (forming a C-terminus amidized polypeptide).

As specific examples of variant maxadilans belonging to the group a), there can be mentioned one represented by SEQ ID NO: 3 (hereafter sometimes referred to as "M42"), one represented by SEQ ID NO: 4 (hereafter sometimes referred to as "M45"), one represented by SEQ ID NO: 5 (hereafter sometimes referred to as "M44B"), and one represented by SEQ ID NO: 6 (hereafter sometimes referred to as "NSP"). On the other hand, as specific examples of variant maxadilans belonging to the group b), there can be mentioned one represented by SEQ ID NO: 7 (hereafter sometimes referred to as "M46"), one represented by SEQ ID NO: 8 (hereafter sometimes referred to as "M48B"), one represented by SEQ ID NO: 9 (hereafter sometimes referred to as "M98"), and one represented by SEQ ID NO: 10 (hereafter sometimes referred to as "M65").

Structural correlation between the above-enumerated variant maxadilans and maxadilan (Max) is shown in FIG. 1. In FIG. 1, the enclosed letters are amino acid residues different than those of maxadilan (Max).

The polypeptides of the invention can be produced, referring to each sequence shown in the sequence listing, according to a peptide synthetic method (see, e.g., New Biochemical Experiment Course, "Protein VI; Synthesis and Expression", edited by Japan Biochemical Society, published by Tokyo Kagaku Dojin, 1992), and a method of using a cloning vector of a gene encoding the desired polypeptide, and further, a method for preparing a deletion variant using the site-specific mutagenesis method on, as a specific example, a gene encoding the amino acid sequence represented by SEQ ID NO: 2, as later described, these method being known per se.

EXAMPLES

The invention is further specifically described below according to examples, but it is not meant that the invention is limited to these examples.

Example 1

Preparation of Tissue Crude Membrane Fraction

The brain of a rabbit (excluding the cerebellum) was homogenized in the following buffer using Polytron PT 3000 (produced by KINEMATICA).

Composition of the Buffer 50 mM Tris-HCl (pH 7.6), 0.32 M sucrose, 5 mM EDTA (ethylenediaminetetraacetic acid), 1 µg/ml leupeptin, 1

μg/ml pepstatin A, 2 μg/ml bacitracin and 10 μg/ml PMSF (phenylmethylsulfonyl fluoride)

The homogenate was low speed centrifuged (1,000×g), the resultant precipitate was homogenized again, the resultant supernatants were combined and high speed centrifuged (30,000×g), and the precipitate was named a crude membrane fraction. The precipitate was suspended in an incubation buffer (buffer obtained by substituting $MgCl_2$ for EDTA in the supernatant buffer), and the suspension was adjusted to a protein concentration of 2,000 mg/ml using the result of protein assay.

Likewise, crude membrane fractions were prepared, respectively, from the brain, liver, pancreas, spleen, aorta and kidney of a rabbit, and the brains of a rat, a mouse, cattle and a human being.

Example 2

Binding Test (Tissue)

Purified maxadilan (see SEQ ID NO: 2) was labeled with $^{125}I$ according to a usual method using chloramine T, and fractionated by HPLC (high performance liquid chromatography : SHIMADZU LC-6A) to obtain a labeled compound having a specific activity of 2,000 Ci/mmol.

70 pM of radioactive maxadilan ($^{125}I$-Max) was incubated at 4° C. for 2 hours together with 400 μg/ml of each crude membrane fraction in the absence or presence of 1 μM of maxadilan. After completion of the reaction, $^{125}I$-Max bound to the membrane was separated by subjecting the resultant incubation matter to suction filtration using a GF/C glass filter (Whatman GF/C), and the radioactivity of the glass filter after being dried was measured by a γ-counter.

Figure 3:
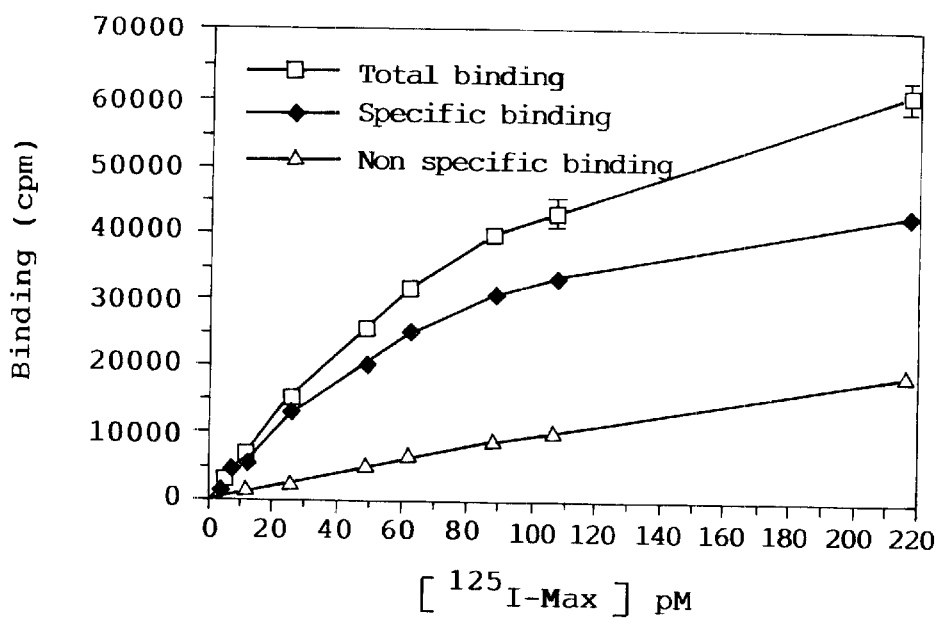
FIG. 3 is a graph showing the characteristic of the binding of maxadilan with change of concentration thereof to the crude membrane fraction from the rabbit brain.
Figure 4:
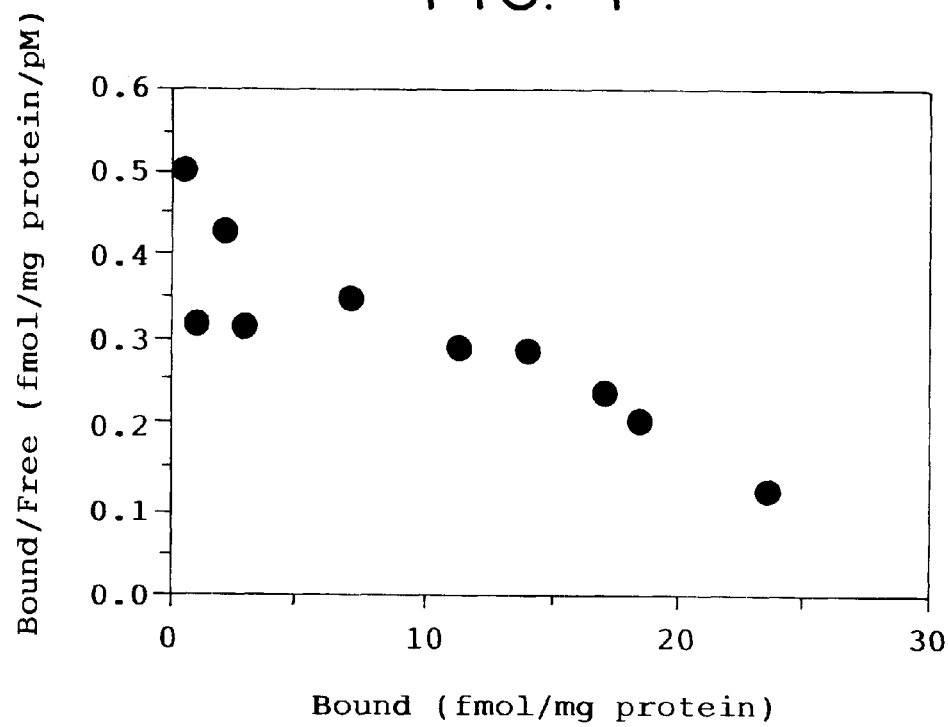
FIG. 4 is a graph showing a Scatchard plot based on the experimental data shown in FIG. 3.

The assay results are shown in FIG. 2 (showing the binding affinity to the crude membrane preparations from the brain and spleen of each animal), FIG. 3 (showing the binding saturation curve of Max to the crude membrane preparation from the rabbit brain), and FIG. 4 (showing the Scatchard plot of the binding of Max to the crude membrane preparation from the rabbit brain).

As shown in FIG. 2, the specific binding of Max is recognized to the crude membrane fractions from the brains of the rabbit and rat and the spleen of the rabbit. Further, the specific binding of Max is also recognized to the crude membrane fractions from the brains of the cattle and the human being. The values in FIG. 2 show the average values and standard deviations of the three times assay results.

As is the case of FIGS. 3 and 4, the dissociation constant (Kd) and the maximum binding amount (Bmax) on each tissue were calculated, from a Scatchard plot and saturation curve prepared using each tissue. All the results are shown in the following Table 1.

TABLE 1

| Species | | Brain | Spleen |
|---|---|---|---|
| Rabbit | Kd | 66 pM | 55 pM |
| | Bmax | 30 fmol/mg | 9 fmol/mg |
| Rat | Kd | 161 pM | |
| | Bmax | 68 fmol/mg | |
| Mouse | Kd | 68 pM | |
| | Bmax | 53 fmol/mg | |
| Cattle | Kd | 66 pM | |
| | Bmax | 17 fmol/mg | |

As apparent from the above results, the binding affinity of maxadilan exhibits species- and tissue-specificity, and the dissociation constant (Kd) of maxadilan at each tissue is much lower than the dissociation constants of CGRP and VIP, which well accords with the fact that maxadilan exhibits a strong vasodilating action.

In this connection, as to each column in FIG. 2, the "Bovine (Brain)" exhibits the binding affinity of $^{125}I$-Max to the bovine brain in the absence and presence of maxadilan (cold), and shows the difference between the value of the bovine brain in the absence of maxadilan (cold) and that of the bovine brain in the presence of maxadilan (cold). Their values are means±standard deviation of triplicate determinations. In the same way, the "Rabbit (Brain)" corresponds to the brain of the rabbit, the "Rat (Brain)" to the brain of the rat, the "Mouse (Brain)" to the brain of the mouse, the "Bovine (Spleen) to the bovine spleen, the "Rabbit (Spleen)" to the rabbit spleen, the "Rat (Spleen)" to the rat spleen, and the "Mouse (Spleen)" to the mouse spleen, respectively.

Example 3

Binding Test (Culture Cell)

The binding affinity of maxadilan to various culture cells was assayed based on each confluent cell in a 6-well plate, each cell was incubated at 4° C. for 2 hours together with 70 pM of $^{125}I$-Max in the absence or presence of 1 μM of maxadilan (cold).

The binding affinity of maxadilan to a human neuroblastoma (NBf1), a rat adrenal medulla melanocytoma (PC-12) and a human neuroblastoma (SK-N-MC) was assayed in the same manner as in the above case where the tissues were used, and as a result, the specific binding affinity thereof was observed to NBf1 and PC-12.

Example 4

Competitive Binding Test

This test was conducted to demonstrate that the receptors confirmed by Examples 2 and 3 are maxadilan-specific.

The crude membrane preparation derived from the rabbit brain, prepared according to Example 1 , was used, and various peptides were assayed for their ability to inhibit the binding of $^{125}I$-Max to the crude membrane preparation. 70 pM of $^{125}I$-Max was incubated with the crude membrane preparation at 4° C. for 2 hours in the presence of 1 μM of each peptide. $^{125}I$-Max bound to the crude membrane preparation was measured according to the method of Example 2. The average value and its standard deviation of the three times experiment results on each peptide were shown in FIG. 5.

Figure 5:
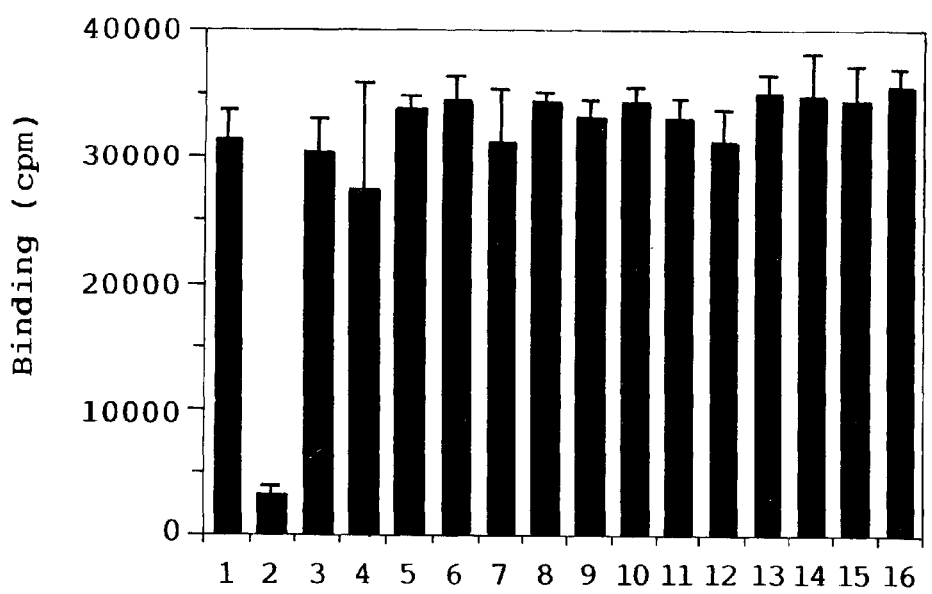
FIG. 5 is a graph showing the competitive binding affinities of other peptides compared with maxadilan binding to the crude membrane fraction from the rabbit brain.

As to the column numbers in FIG. 5, 1 shows (control: absence of peptide), 2 (maxadilan: cold), 3 (VIP), 4 (CGRP), 5 (amylin), 6 (neurotensin), 7 (brady-kinin), 8 (bombesin), 9 (oxytocin), 10 (somatostatin), 11 (angiotensin II), 12 (parathyroid hormone), 13 (substance P), 14 (endothelin I), 15 (endothelin II) and 16 (endothelin III), respectively.

It is understood from FIG. 5 that the receptor in the crude membrane preparation is maxadilan-specific.

Likewise, any of carbamylcholine chloride, 3-hydroxytyramine, 5-hydroxytryptamine, histamine dihydrochloride, GABA, isoproterenol, arterenol, glycine and glutamate, which are non-peptide compounds and known as intracerebral signal mediators, and verapamil and nifedipine, which are pharmaceuticals acting on the ion channel did not inhibit the binding of maxadilan to the crude membrane preparation.

From the results of a competitive inhibition test using peptides acting on the blood vessel, the pharmaceuticals acting on the brain and the pharmaceuticals acting on the ion channel, the possibility that the receptor in the crude membrane preparation is maxadilan-specific is extremely high.

Example 5

Investigation of Second Messenger

On the NBf1 cell and PC-12 cell on which the specific binding of $^{125}$I-Max was observed in the binding test of Example 3, the production amount of cAMP by maxadilan was checked.

Figure 6:
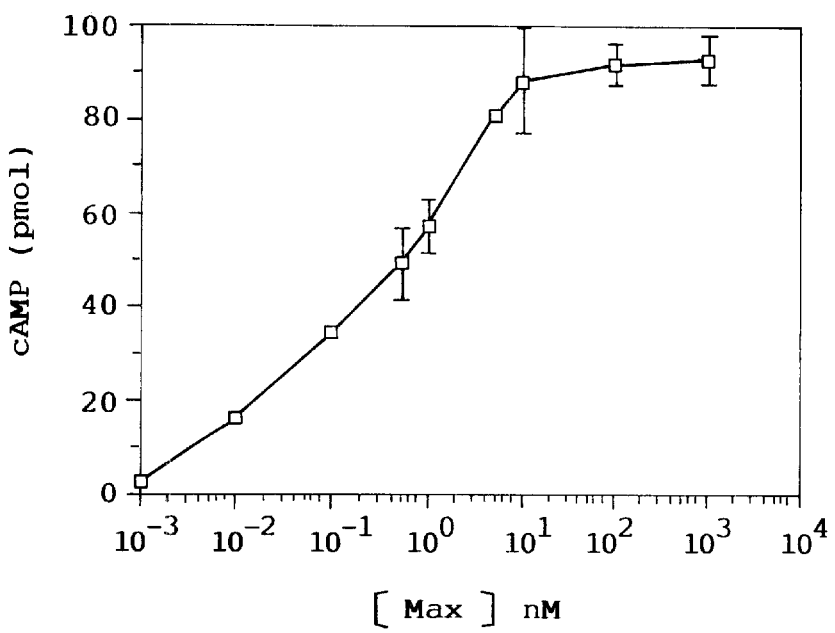
FIG. 6 is a graph showing the characteristic of cAMP production in the rat adrenal medulla melano-cytoma PC-12 cell in the presence of maxadilan (concentration change)

Namely, the PC-12 cell ($1\times10^6$) was incubated at 37° C. for 10 minutes in the presence of maxadilan in various concentrations, and then, cAMP in the cell was assayed. The assay of cAMP was conducted using a cAMP-assaying ELISA kit (Amersham) and according to the operating manual therefor. The results are shown in FIG. 6. As is seen in FIG. 6, the dose-dependency of maxadilan is observed on the production amount of cAMP, and thus maxadilan significantly promotes cAMP production by the culture cell.

Then, the change of cAMP production amount with time lapse after stimulation with maxadilan was assayed. Namely, the cell was incubated at 37° C. for various time in the presence of 100 nM of maxadilan, and then, the amount of cAMP in the culture cell was assayed. The results are shown in FIG. 7.

Figure 7:
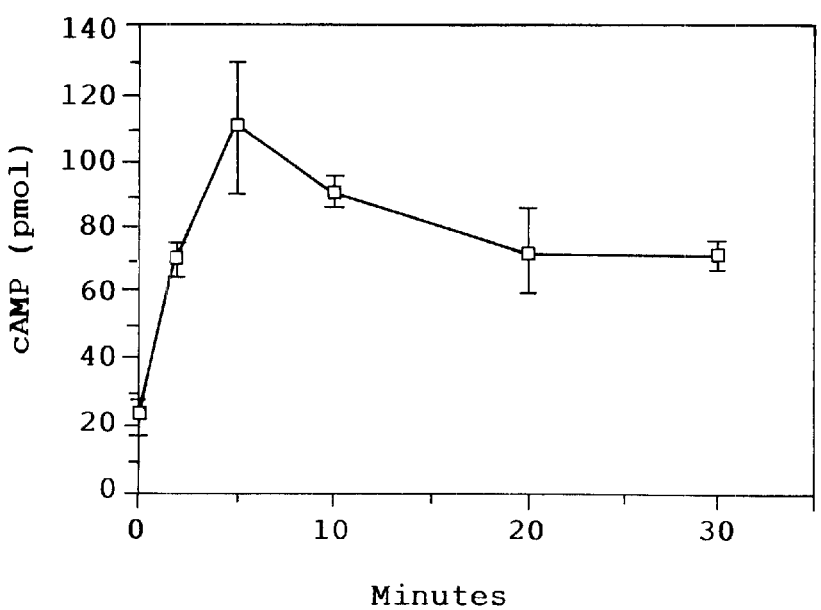
FIG. 7 is a graph showing the characteristic of cAMP production with time lapse in the the above PC-12 cell in the presence of maxadilan.

It is seen from FIG. 7 that cAMP production by maxadilan stimulation is conducted in an instant, and thereby, it is suggested that the maxadilan receptor is coupled to the adenyl cyclase activity-promoting system. The above results were also likewise observed in the NBf1 cell and a rat pancreas smooth muscle MILE cell.

Example 6

Activity of Variant Maxadilan (1) Binding Inhibition Test

The rabbit brain crude membrane fraction prepared according to the method of Example 1 was used.

100 pM of radioactive maxadilan ($^{125}$I-Max) and a variant maxadilan of various concentrations were incubated together with 400 μg/ml of the rabbit brain crude membrane fraction at 4° C. for 2 hours. After completion of the reaction, $^{125}$I-Max bound to the membrane and the free $^{125}$I-Max were separated by subjecting the resulting incubation matter to suction filtration using a GF/C glass filter, and the radioactivity of the glass filter after being dried was measured by a γ-counter.

The variant maxadilans used for the assay were M42 (SEQ ID NO: 3), M45 (SEQ ID NO: 4), M44B (SEQ ID NO: 5), NSP (SEQ ID NO: 6), M46 (SEQ ID NO: 7), M48B (SEQ ID NO: 8), M98 (SEQ ID NO: 9), M65 (SEQ ID NO: 10), M67 (SEQ ID NO: 11) and M64 (SEQ ID NO: 12).

Figure 8:
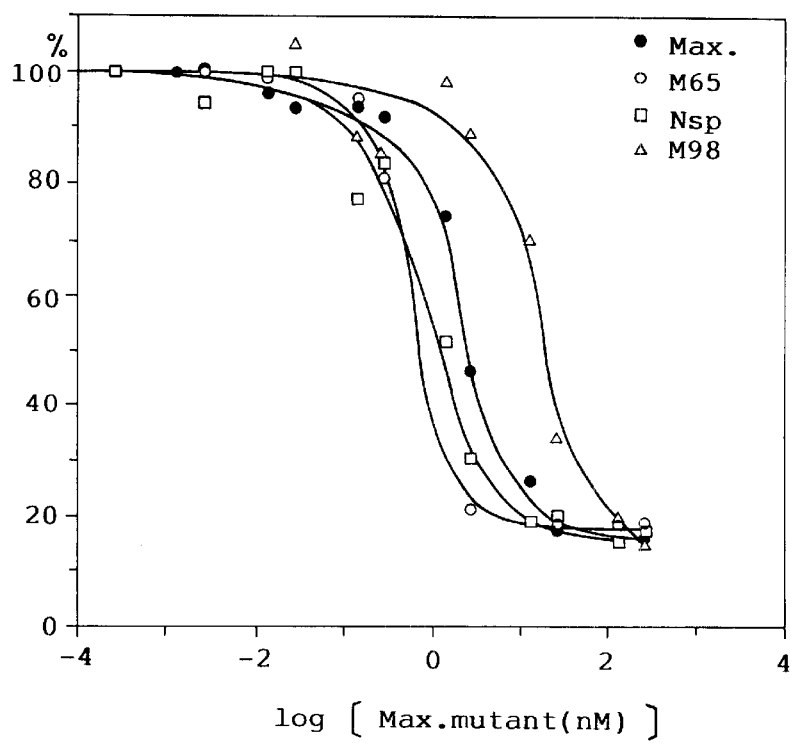
FIG. 8 is a graph showing the competitive binding affinity of the variant maxadilans (M65, Nsp, M98) on maxadilan binding to the crude membrane fraction from the rabbit brain.
Figure 9:
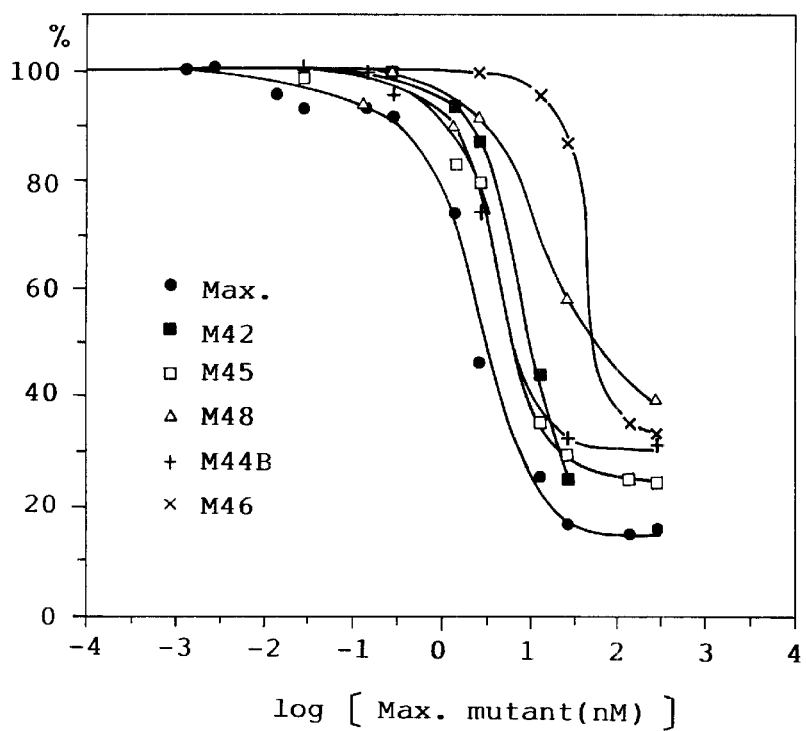
FIG. 9 is a graph showing the competitive binding affinity of the variant maxadilans (M42, M45, M48, M44B, M46) on maxadilan binding to the crude membrane fraction from the rabbit brain.

The assay results concerning the main variant maxadilans are shown in FIG. 8 and FIG. 9.

It is seen that M67 and M64 do not exhibit binding inhibition ability, but the other variant maxadilans concentration-dependently inhibit the binding of $^{125}$I-Max. All $IC_{50}$ (50% binding inhibition concentration) values as an index of binding inhibition ability are shown in Table 2.

(2) cAMP Production Test

A rat adrenal medulla melanocytoma PC-12 ($1\times10^6$ cells) cultured on a 24-well plate was cultured at 37° C. for 10 minutes in a serum-free medium in the presence of each variant maxadilan. The assay of cAMP was conducted using a cAMP-assaying ELISA kit (Amersham).

Figure 10:
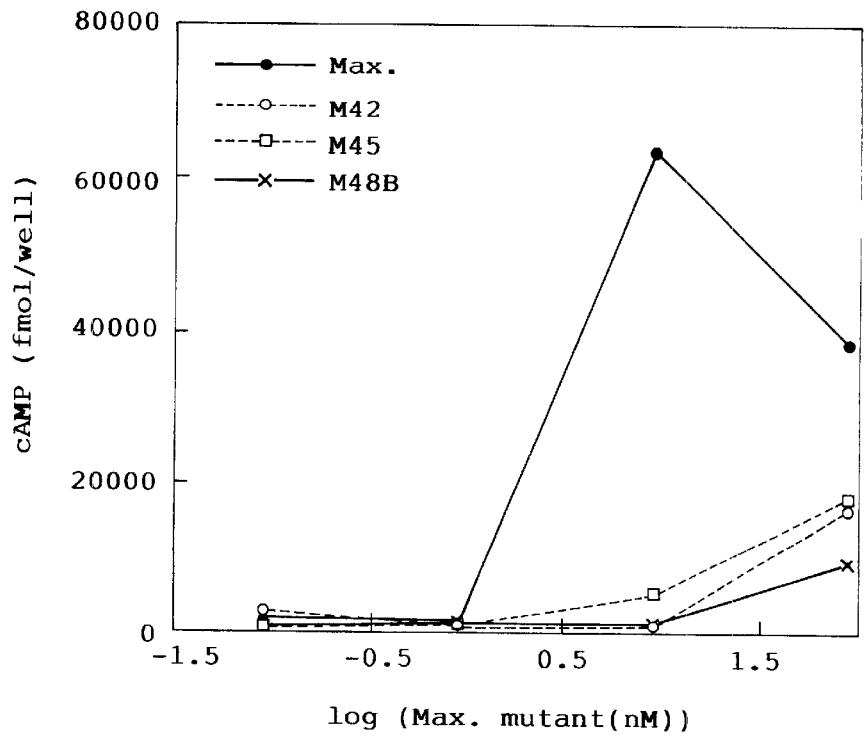
FIG. 10 is a graph showing the characteristic of cAMP production in the the above PC-12 cell in the presence of variant maxadilans (M42, M45, M48)
Figure 11:
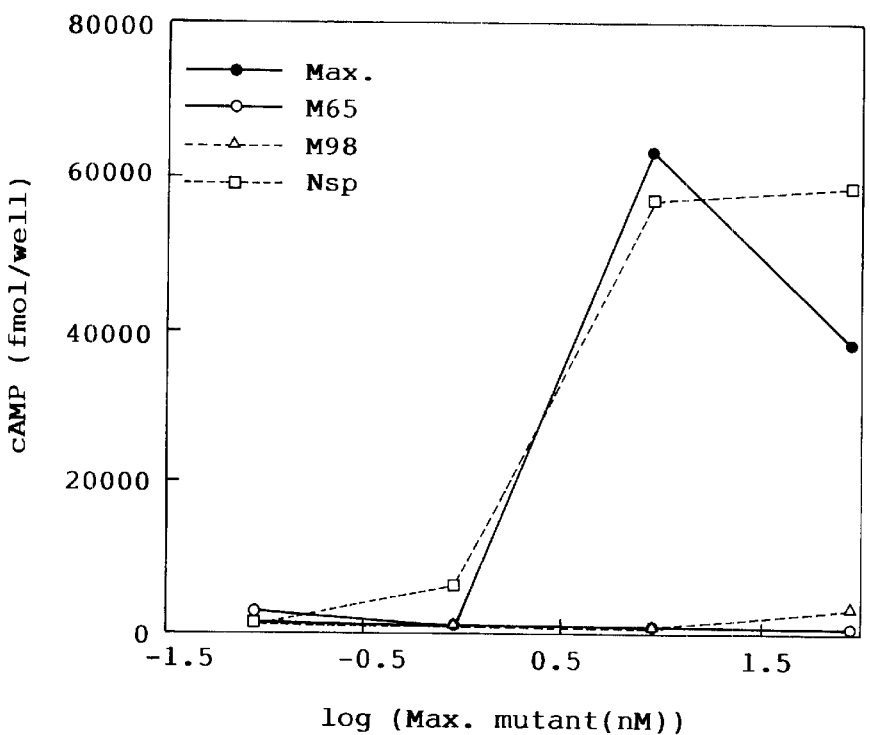
FIG. 11 is a graph showing the characteristic of cAMP production in the the above PC-12 cell in the presence of variant maxadilans (M65, M98, Nsp)

The assay results are shown in FIG. 10 and FIG. 11.

(3) Vasodilation Test

Erythema formation activity on rabbit skin was evaluated according to the method described in Lerner et al., J. Bio. Chem. Vol. 267, 1063 (1992). More specifically, 50 μl portions of dilutions of each sample at various concentrations in physiological saline were intracutaneously injected into white rabbits whose hair was shaved. Erythema formed on the skin of the rabbits was observed 30 minutes and 2 hours after the injection.

All the results are shown in the following Table 2.

TABLE 2

| Variant maxadilan | $IC_{50}$ | Erythema formation activity |
|---|---|---|
| Max (Comparison) | 3.6 nM | $10^{-12}$ |
| M42 | 11.6 nM | $10^{-10}$ |
| M45 | 9.2 nM | $10^{-10}$ |
| M44B | 13.2 nM | $10^{-10}$ |
| M48B | 124.1 nM | $>10^{-6}$ |
| M46 | 92.3 nM | $>10^{-6}$ |
| NSP | 2.0 nM | $10^{-12}$ |
| M65 | 1.7 nM | $>10^{-6}$ |
| M64 | $>1$ μM | $>10^{-6}$ |
| M67 | $>1$ μM | $>10^{-6}$ |

It is seen from Table 2 that the variant maxadilans wherein referring to SEQ ID NO: 1, its Cys (1) to Cys (5) are deleted, or any of Cys (1) and Cys (5) is replaced by another amino acid, but the sequence of Gln (6) to Ala (61) is conserved (M42, M45, M44B, NSP), act on the maxadilan receptor as an agonist. On the other hand, it is also seen that the variant maxadilans wherein referring to SEQ ID NO: 1, its Leu (24) to Leu (43) at most are deleted, or at least one of Cys (14) and Cys (51) is replaced by other amino acid(s) (M65, M48B, M46), act on the maxadilan receptor as an antagonist.

Although it is not intended to be restricted by the theory, the following reasoning is possible by further making consideration taking the secondary structure of Max (see FIG. 12) surmised by applying the above actions to the formula of Chou and Fasman.

The N-terminal ring structure (Cys (1) to Cys (5)) corresponding to the active site of CGRP surmised to have an analogous secondary structure, is not always necessary for variant maxadilans to act as an agonist, but it is necessary therefor that the variant maxadilans have the two α-helix structure parts and the β-sheet structure part together. On the other hand, variant maxadilans in which either the β-sheet structure part is deleted, or Cys (14) and Cys (51) existing in the two α-helix structure parts are replaced by other amino acids, act as an antagonist.

Representative examples of preparation of variant maxadilans provided by the invention are described below. Those not specifically described there in can also be prepared either by modifying the methods described therein, by a chemical peptide synthesis method, or by other peptide variation method known per se.

Example 7

Figure 13:
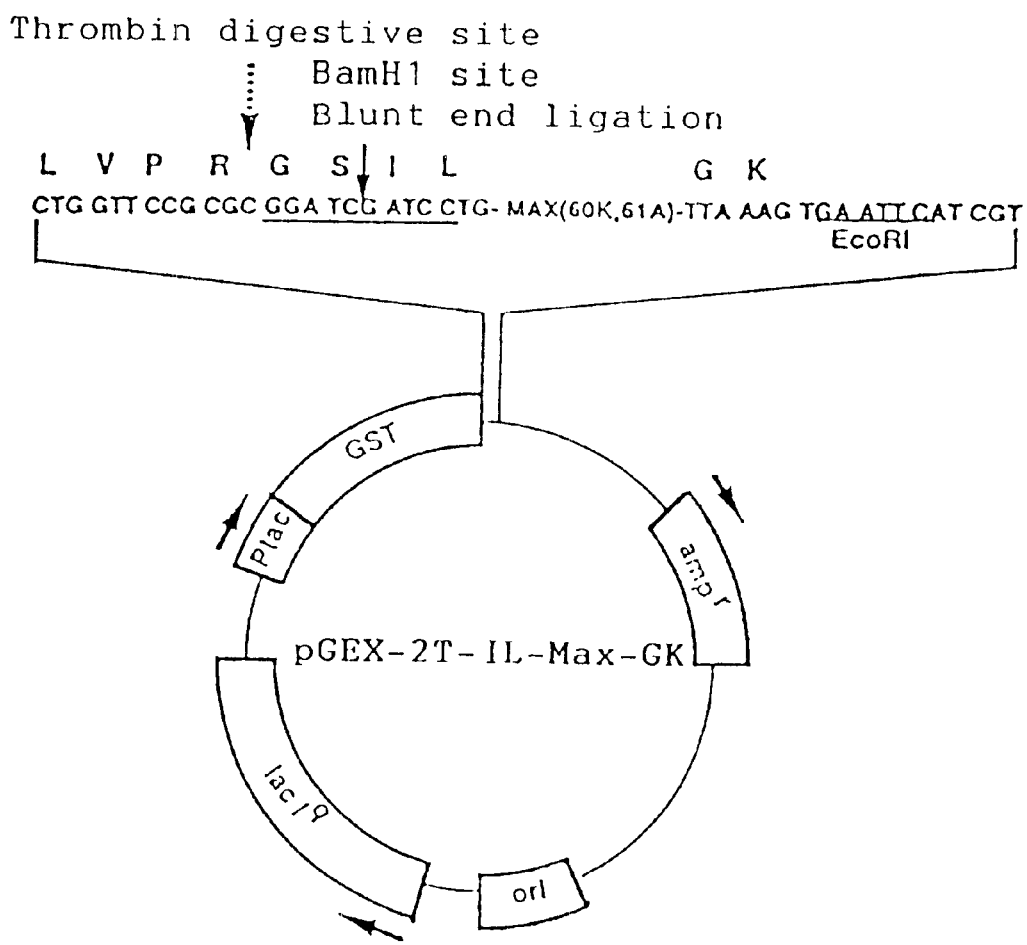
FIG. 13 is a schematic drawing of the expression vector of the maxadilan gene.
Figure 16:
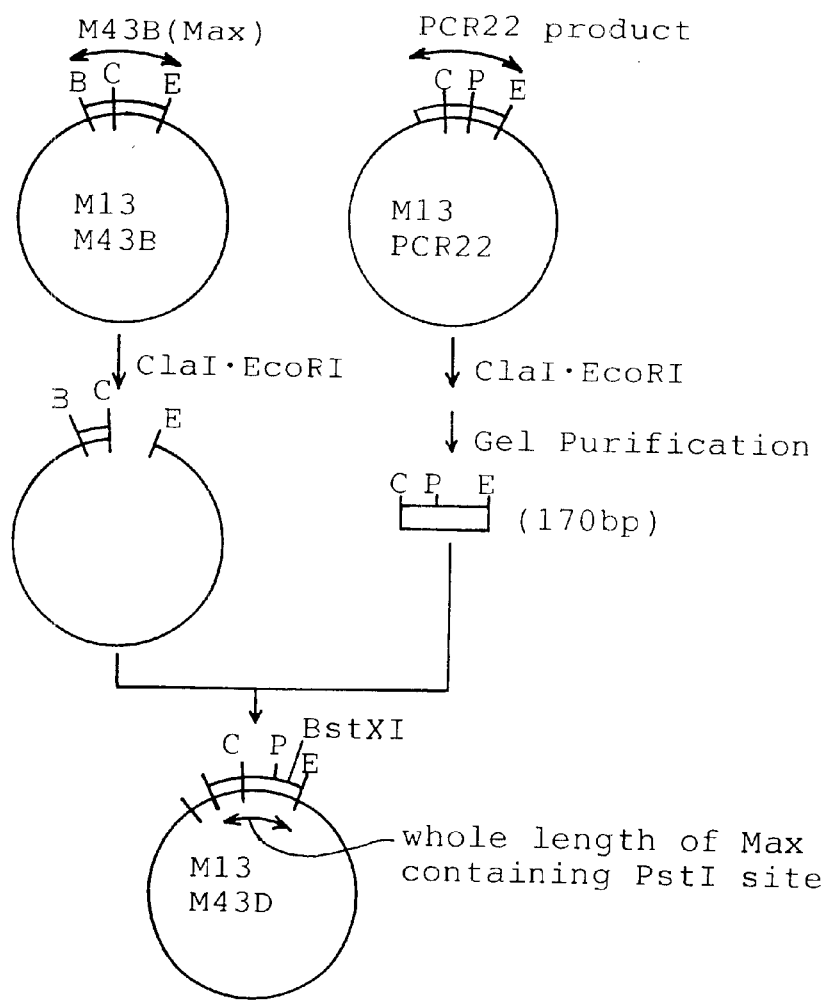
FIG. 16 is a process drawing for construction of a vector M13-M43D.
Figure 17:
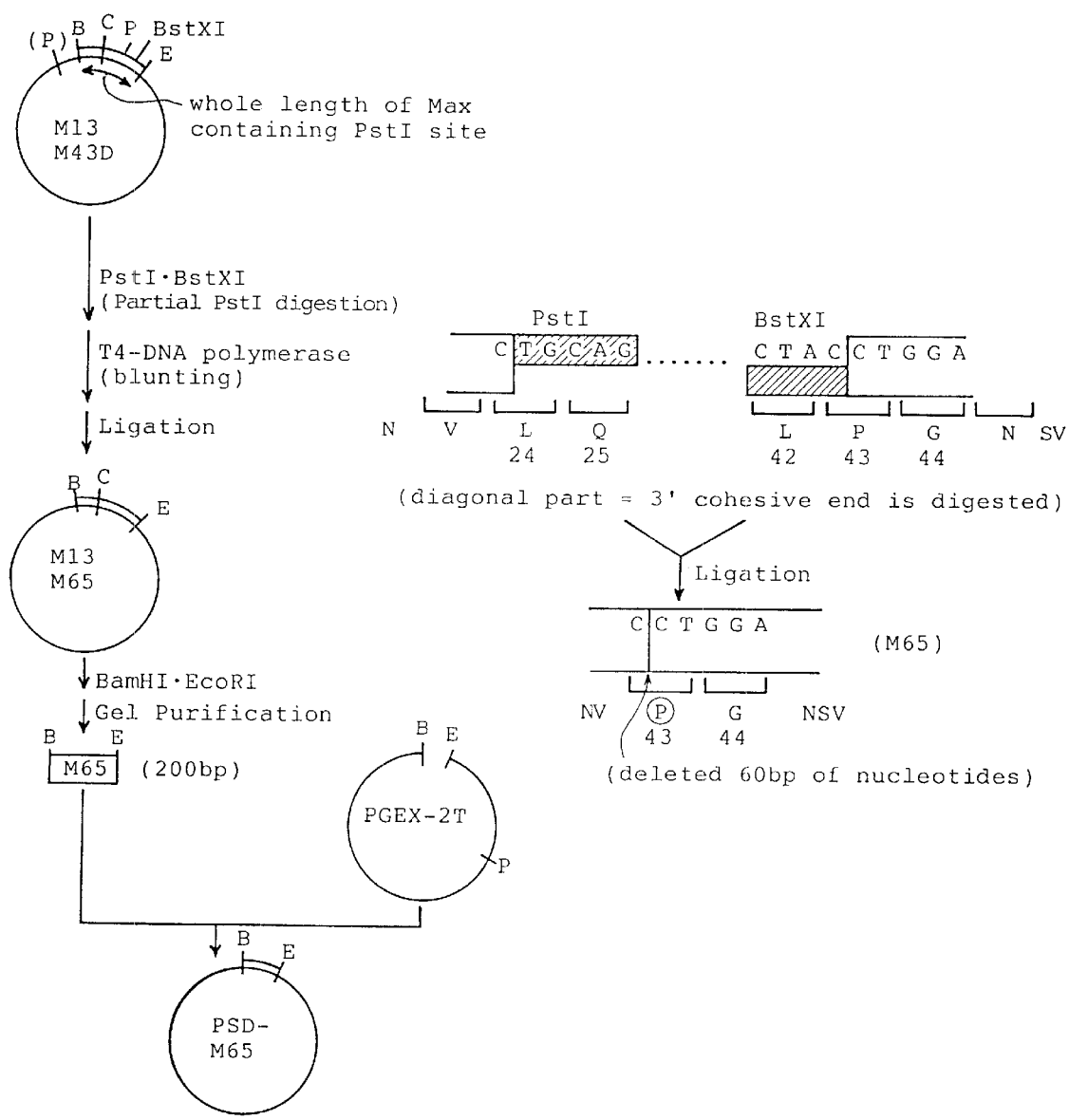
FIG. 17 is a process drawing for construction of an expression vector pSD-M65.

Production of M65
Preparation of M65 Expression Vector (pSD-M65)
  1) Construction of pGEX-2T-IL-Max According to the method described in the above E. A. Lerner et al., J. Bio. Chem. 267, 1062–1066 (1992), the cDNA sequence (a gene encoding the Cys (1) to Ala (61) sequence of SEQ ID NO: 1; abbreviated as "MAX (60K, 61A)") of maxadilan was inserted into an expression vector pGEX-2T (Pharmacia) to give pGEX-2T-IL-Max-GK. This expression vector is schematically shown in FIG. 13. Succeeding steps are given in FIGS. 14 to 17.

2) Preparation of M13-M43B

The introduction of site-directed mutagenesis was conducted according to the polymerase chain reaction (PCR) method using pGEX-2T-IL-Max-GK as a template.

In this PCR method, GS-AsCl (45 mer) (SEQ ID NO: 13) represented by the following formula

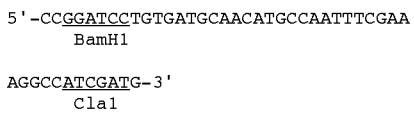

was used as a 5' primer, and KAGK (28 mer) (SEQ ID NO: 14) represented by the following formula

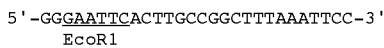

was used as a 3' primer. In an Astec PC-700 program-type constant temperature bath, thermal denaturation at 94° C. for one minute, annealing of the primers at 55° C. for one minute, and then DNA synthesis at 72° C. for 2 minutes were conducted for 30 cycles. The composition of the reaction solution was 0.1 pmol of the template DNA, 200 µM of dNTP, 50 pmol each of 5' and 3' primers, 2.5 U of Taq polymerase (Takara Shuzo) and buffer for the Taq polymerase (Takara Shuzo) (Total 100 µl).

The thus obtained PCR reaction product was cleaved with restriction enzymes BamH1 and EcoR1, separation was conducted by agarose gel electrophoresis, and the resultant 200 bp fragment (PCR-amplified part) was purified from the gel. The fragment was ligated to a subcloning vector M13mp10, the resultant vector was introduced into E. coli JM105, and the RF (double-strand) DNAs and single-strand DNAs of the resultant transformed clones were prepared. Base sequencing of the single-strand DBA was conducted, and clones containing the desired DNA were selected. The base sequencing was conducted by the M13 dideoxy method (Toyobo, Sequenase Kit), and analysis was conducted using Hitachi DNA sequencer. Thus, substitution of the base sequence was conducted without changing the amino acid sequence to give M13-M43B in which restriction enzyme Cla1 cleavage sites are introduced.

3) Preparation of M13-PCR22

Introduction of site-directed mutagenesis was conducted according to the PCR method using RF DNA of M13-M43B as a template.

In this PCR method, C-P (47 mer) (SEQ ID NO: 15) represented by the following formula

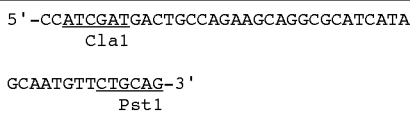

was used as a 5' primer, the above KAGK (28 mer) was used as a 3' primer, and PCR was conducted under the above conditions.

The PCR product was treated with T4 DNA polymerase to blunt end of the DNA and cleaved with EcoR1, and the resultant 170 bp fragment was purified by agarose gel electrophoresis. The fragment was ligated to a vector M13mp10 (one in which the multi-cloning site is cleaved with Sma1 and EcoR1), the resultant vector was introduced into E. coli JM105, and the RF (double-strand) DNAs and single-strand DNAs of the resultant transformed clones were prepared. Base sequencing of the single-strand DNAs was conducted, and clones containing the desired DNA were selected.

Thus, M13-PCR22 was obtained in which restriction enzyme Pst1 cleavage sites were introduced without changing the amino acid sequence in the neighborhood (Leu (24), Gln (25)) of the boundary line between the N-terminal α-helix and β-sheet in the surmised secondary structure of maxadilan. Due to restriction of the length of the 5' primer (synthesis of a primer DNA of 50 bp or longer is difficult), the sequence from the N-terminus to the Cla1 site of maxadilan was removed.

4) Preparation of M13-M43D

Since the thus obtained M13-PCR22 lacks the sequence from the N-terminus to the Cla1 site of Max, M13-PCR22 and the sequence from the N-terminus to the Cla1 site of Max were ligated at the Cla1 site to give Max in full length.

Specifically, RF DNA of M13-PCR22 was cleaved with Cla1 and EcoR1, and the resultant 170 bp fragment (from the Cla1 site to the C-terminus; containing a Pst1 site) was purified by agarose gel electrophoresis. The fragment was ligated to M13-M43B (one cleaved with Cla1 and EcoR1; a vector containing the sequence from the N-terminus to the Cla1 site of Max), the resultant vector was introduced into E. coli JM105, and RF DNAs of the resultant transformed clones were prepared.

5) Preparation of M13-M65

A sequence (one between the Pst1 site and the BstX1 site) corresponding to the β-sheet part of Max was removed from M13-M43D, and the residual product was ligated so as to make the frame appropriate.

Specifically, RF DNA of M13-M43D was partially (so as to cleave only one of the two sites) cleaved with Pst1, further cleaved with BatX1, and the resultant cut end (3' cohesive end) was digested with DNA polymerase to blunt it. The blunt ends were self-ligated to conduct cyclization, the resultant vector was introduced into E. coli JM105, and then the RF DNAs and single-strand DNAs of the resultant transformed clones were prepared. Base sequencing of the single-strand DNAs was conducted, and clones containing the desired DNA were selected.

6) Preparation of pSD-M65

DNA of M13-M65 containing the desired sequence was integrated into an expression vector pGEX-2T.

Specifically, RF DNA of M13-M65 was cleaved with BamH1 and EcoR1, the resultant 140 bp fragment (M65 gene in full length) was purified by agarose gel electrophoresis. The fragment was ligated to a vector pGEX-2T, and the resultant vector was introduced into E. coli HB101. Thus, E. coli HB101 transformed with the expression vector pSD-M65 for M65 was obtained.

The PCR method, the genetic recombination method, the transformation method, etc. in the stages of the above 1) to 6) can be conducted by standard methods therefor known per se, but if necessary, see Genetic Engineering Handbook, Experimental Medicine Separate Volume, published by Yodo-Sha, 1991.

Production of M65

E. coli HB101 transformed with pSD-M65 was cultured and grown at 37° C. for 3 hours in LB medium. One mM of isopropyl-β-D-thiogalactopyranoside (IPTG) per $10^9$ cells was added to the medium at the logarithmic phase of the strain to induce production of the GST-M65-used protein, and culture was continued for further 5 hours.

The cells were collected by centrifugation, washed with PBS, and ultrasonicated to fracture them. The treatment product was centrifuged (8,000 rpm, 10 minutes) to give the supernatant. The supernatant contained about 5% of the desired protein per the whole proteins in the cells. This supernatant was treated with a GST-affinity column (glutathione-Sepharose 4B, Pharmacia) to isolate the GST-M65-fused protein. 10 μg per ml of thrombin (Mochida Pharmaceutical) was added to solution of 50 mM Tris HCl (pH 8.0), 150 mM NaCl and 2.5 mM $CaCl_2$ containing 2 mg/ml of the GST-M65-fused protein, and incubation was conducted at 37° C. for one hour. The treatment solution was treated with a GST-affinity column (above-mentioned), and the detached M65 was eluted. The eluate was treated with reverse-phase HPLC [CAPCELL PAK C8• SG300, 6×35 mm, Shiseido, eluent: 0.1% trifluoroacetic acid-water/ acetonitrile (1–60%)]. The protein fractions were detected at an absorbance of 214 nm, and the desired fractions were combined and freeze-dried.

The resultant polypeptide M65 was identified for its purity and molecular weight by SDS-PAGE (10 to 20% gel), the whole amino acid sequence except Cys was determined by a peptide sequencer (AB1471A), and it was confirmed that M65 consists of the following amino acid sequence (see SEQ ID NO: 10). Its molecular weight was determined to be 4237 by MALDI (mass spectrum).

GS-CDATCQFRKAIDDCQKQAHHSNV-PGNSVFKECMKOKKKEFKAGK

Production of M98

M98 has the amino acid sequence represented by SEQ ID NO: 9.

Figure 18:
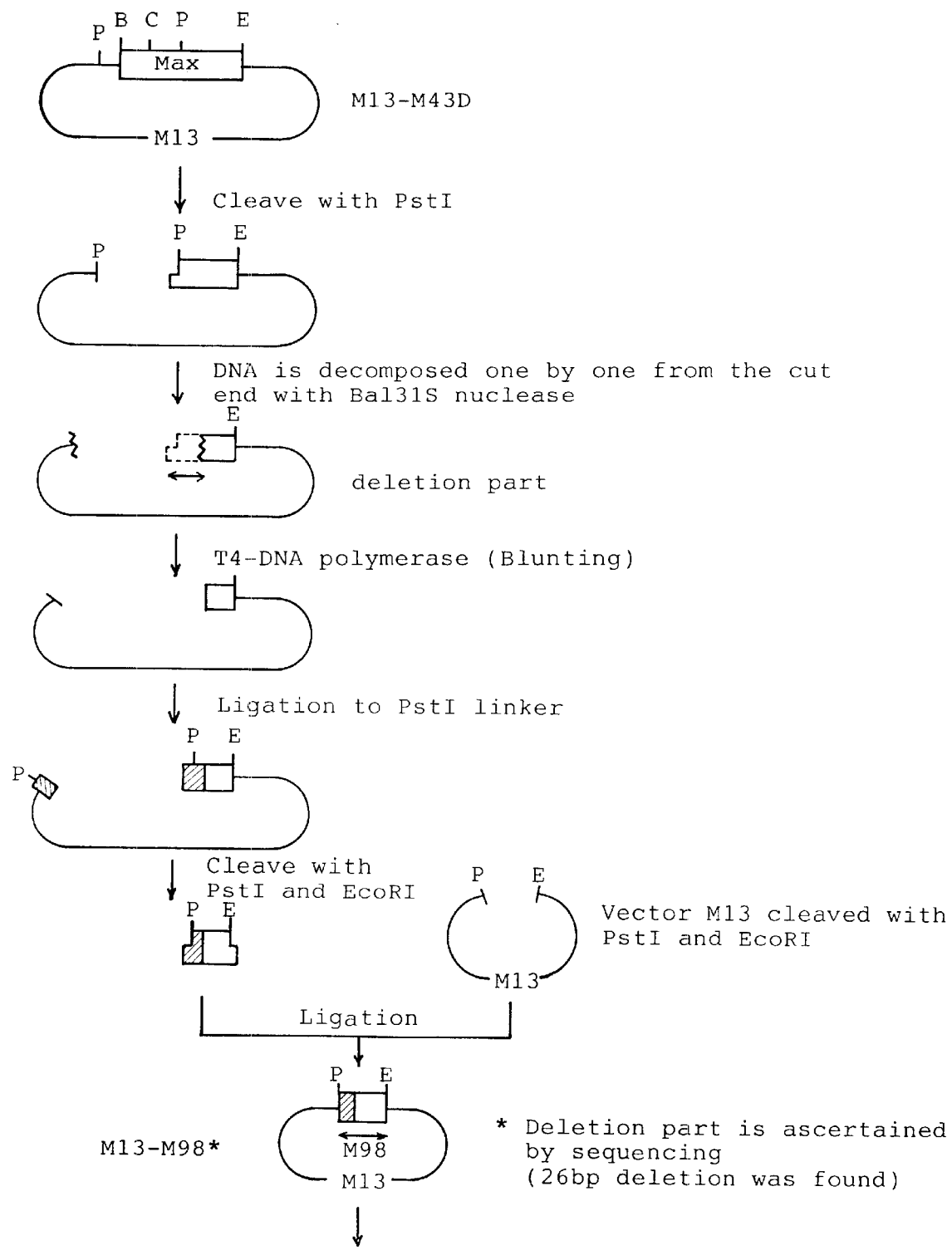
FIG. 18 is a process drawing for construction of a vector M13-M98.

An expression vector for M98 can be constructed according to the procedure shown in FIG. 18 and FIG. 19, using the thus obtained subcloning vector M13-M43D and an expression vector pSD-M65. M98 was obtained by introducing the resultant expression vector into *E. coli* HB101, culturing the resultant transformant according to the same method as adopted in the production of the above M65, treating the cells, and isolating the desired polypeptide.

Production of Nsp

Nsp has the amino acid sequence of SEQ ID NO: 6.

Figure 20:
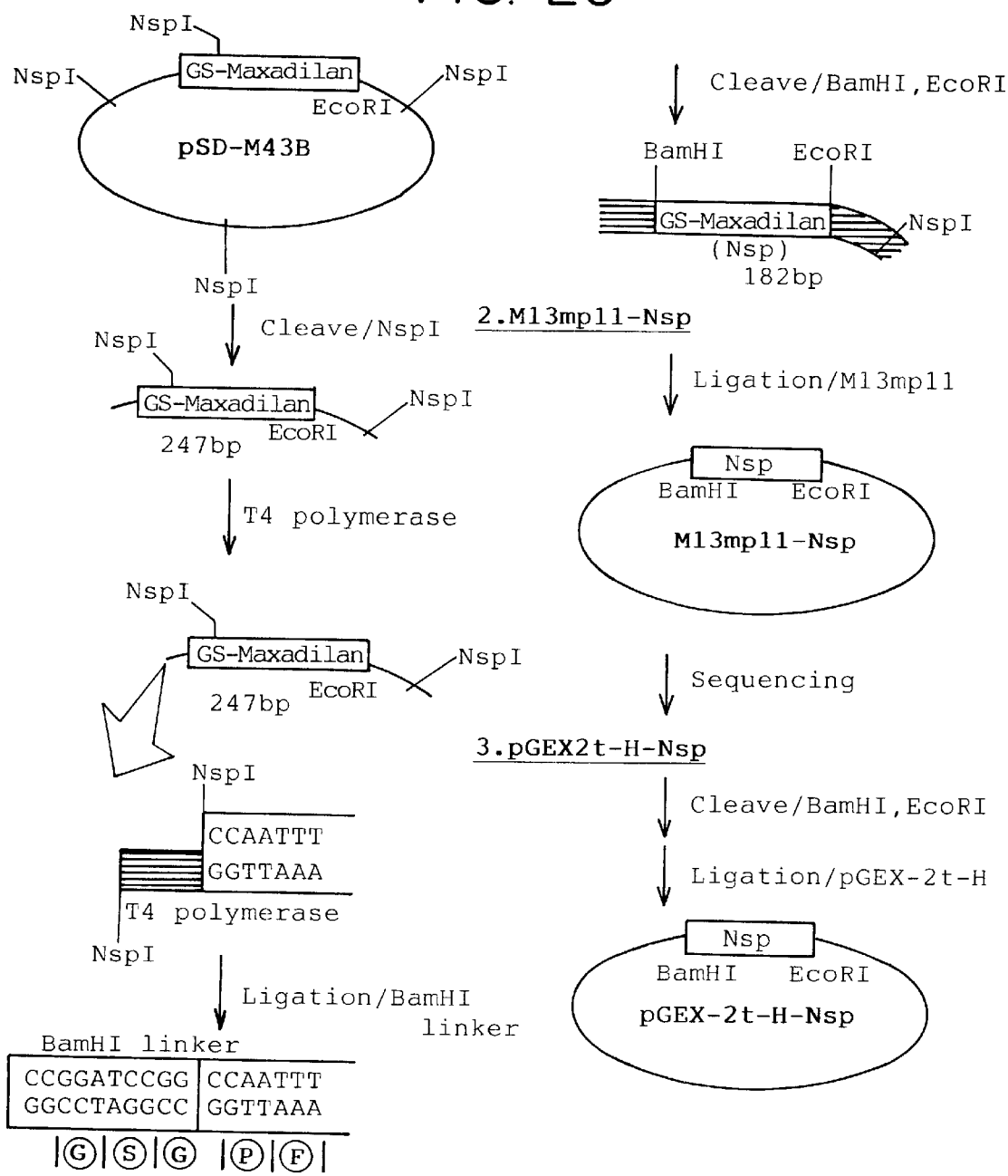
FIG. 20 is a process drawing for preparation of the Nsp fragment.

1) Preparation of Nsp fragment (see FIG. 20)

0.5 mg of pSD-M43B vector constructed in the above manner was cleaved with a restriction enzyme Nsp1, and the resultant reaction product was treated with DNA Blunting Kit (Takara Shuzo) to blunt the 3' cohesive end. This was separated by agarose electrophoresis, and an about 250 bp fragment was purified from the gel.

2) Preparation of M13mp11-Nsp

The above fragment was ligated to a BamH1 linker (Takara Shuzo)

3 '-d(pCCGGATCCGG )-5'(SEQ ID No:17)

and the ligation product was cleaved with restriction enzymes BamH1 and EcoR1. This was separated by agarose gel electrophoresis, and an around 180 bp fragment was purified from the gel. This was ligated to a vector M13mp11 (one cleaved with BamH1 and EcoR1 in the multi-cloning site), the resultant vector was introduced into *E. coli* JM105, and the base sequence of DNA of the transformed clone was confirmed. Nucleotide sequencing was conducted by the M13 dideoxy method (Toyobo Sequencing Kit), and analysis was conducted by Hitachi Fluorescent DNA sequencer.

3) Preparation of pGEX-2t-H-Nsp

The DNA of M13mp11-Nsp, which turned out to have the desired sequence, was recombined into an expression vector pGEX-2t-H.

*E. coli* HB101 transformed with pGEX-2t-H-Nsp was cultured at 37° C. for 3 hours in LB medium. One mM of isopropyl-β-D-galactoside (IPTG) was added to the medium at the logarithmic phase of the strain to induce production of the GST-Nsp-fused protein, and culture was continued for further 5 hours.

The cells were collected by centrifugation, and ultrasonicated to fracture them. The resultant treatment matter was centrifuged at 12,000 rpm for 20 minutes, and the resultant supernatant was added to glutathione-Sepharose 4B (Pharmacia). Thrombin treatment was conducted in the column, and elution was conducted to give a detached Nsp crude fraction. The eluate was purified by reverse HPLC (CAPCELL PAK C8•SG300, 6×35 mm, Shiseido).

The resultant polypeptide Nsp was checked for purity and molecular weight by SDS-PAGE gel, and then confirmation of up to 20th amino acid from the N-terminus was conducted by a peptide sequencer (AB1471A). Its molecular weight was confirmed by MALD1 (mass spectrum).

What is claimed is:

1. An isolated polypeptide which specifically binds to a receptor which maxadilan specifically binds, said polypeptide being selected from the group consisting of:
   a) a polypeptide comprising the amino acid sequence of Cys (1) to Ala (61) of SEQ ID No. 1, wherein at least one of the amino acid residues of Cys (1) to Cys (5) is deleted,
   b) a polypeptide comprising the amino acid sequence of Cys (1) to Ala (61) of SEQ ID No. 1, wherein at least one of the amino acid residues Cys (1) and Cys (5) is replaced by an amino acid(s) other than Cys,
   c) a polypeptide comprising the amino acid sequence of Cys (1) to Ala (61) of SEQ ID No. 1, wherein at least one of the amino acid residues of Leu (24) to Gly (44) is deleted, and
   d) a polypeptide comprising the amino acid sequence of Cys (1) to Ala (61) of SEQ ID No. 1, wherein at least one of the amino acid residues of Cys (14) and Cys (51) is replaced by an amino acid(s) other than Cys.

2. The polypeptide according to claim 1, which specifically binds to a receptor which maxadilan specifically binds, and promotes the production of cAMP in an animal culture cell to which maxadilan specifically binds, said cell having a cAMP production ability.

3. The polypeptide according to claim 1, which specifically binds to a receptor which maxadilan specifically binds, but does not promote the production of cAMP in an animal culture cell to which maxadilan specifically binds, said cell having a cAMP production ability.

4. The polypeptide according to claim 1, wherein a peptide fragment selected from the group consisting of (i) Gly-Ile-Leu-(SEQ ID No. 16), (ii) Gly-Ile-, (iii) Gly-Ser-, (iv) Gly-Ser-Gly- and (v) Gly-Ile-Leu- is bound to the N-terminal amino acid of each of said polypeptides a) to d) and either -Gly-Lys is bound to the C-terminal amino acid of each of said polypeptides a) to d), or the carboxyl group of the C-terminal amino of each of said polypeptides a) to d) is converted to a carbamoyl group.

5. The polypeptide according to claim 1, which is represented by SEQ ID No: 3, SEQ ID No: 4, SEQ ID No: 5, SEQ ID No: 6, SEQ ID No: 8, SEQ ID No: 9 or SEQ ID No: 10.

6. The polypeptide according to claim 1, which is represented by SEQ ID No: 3, SEQ ID No: 4, SEQ ID No: 5 or SEQ ID No: 6.

7. An isolated polypeptide which specifically binds to a receptor which maxadilan specifically binds, said polypeptide being selected from the group consisting of:
   a) a polypeptide consisting of the amino acid sequence of Gln(6) to Ala (61) of SEQ ID No. 1, b) a polypeptide consisting of the amino acid sequence of Cys (1) to Thr (4) and Gln (6) to Ala (61) of SEQ ID No. 1 in this order, c) a polypeptide consisting of the amino acid sequence of Asp (2) to Ala (61) of SEQ ID No. 1, d) a polypeptide consisting of the amino acid sequence of Asp (2) to Thr (4) and Gln (6) to Ala (61) of SEQ ID No. 1 in this order, e) a polypeptide consisting of the amino acid sequence of Cys (1) to Ala (61) of SEQ ID No. 1, wherein at least one of the amino acid residues of Cys (1) and Cys (5) is replaced by an amino acid(s) other than Cys, f) a polypeptide consisting of the amino acid sequence of Cys (1) to Val (23) and Pro (43) to Ala (61) of SEQ ID No. 1 in this order, g) a polypeptide consisting of the amino acid sequence of Cys (1) to Val (23) and Pro (43) to Ala (61) of SEQ ID No. 1 and at most eight consecutive amino acid residues of Leu (24) to Leu (42) of SEQ ID No. 1 in between Val (23) and Pro (43), and h) a polypeptide consisting of the amino acid sequence of Cys (1) to Ala (6 1) of SEQ ID No. 1, wherein at least one of the amino acid residues of Cys (14) and Cys (51) is replaced by an amino acids(s) other than Cys.

8. The polypeptide according to claim 7, wherein a peptide fragment selected from the group consisting of (i) Gly-Ile-Leu-(SEQ ID No. 16), (ii) Gly-Ile-, (iii) Gly-Ser-, (iv) Gly-Ser-Gly- and (v) Gly-Ile-Leu- is bound to the N-terminal amino acid of each of said polypeptides a) to h), and either -Gly-Lys is bound to the C-terminal amino acid of each of said polypeptides a) to h), or the carboxyl group of the C-terminal amino of each of said polypeptides a) to h) is converted to a carbamoyl group.

9. The polypeptide according to claim 8, wherein the peptide fragment selected from the group consisting of (i) Gly-Ser-Ile-Leu- (SEQ ID No. 16), (ii) Gly-Ile-, (iii) Gly-Ser-, (iv) Gly-Ser-Gly- and (v) Gly-Ile-Leu- is bound to the $\alpha$-amino group of the N-terminal amino acid of each of said polypeptide a) to h).

10. The polypeptide according to claim 8, wherein the peptide fragment -Gly-Lys or an amino group is bound to the carboxyl group of the C-terminal amino acid of each of said polypeptides a) to h).

11. The polypeptide according to claim 1, said receptor is in a tissue preparation derived from a mammal.

12. The polypeptide according to claim 2, wherein said receptor is in a tissue preparation derived from a mammal.

13. The polypeptide according to claim 3, wherein said receptor is in a tissue preparation derived from a mammal.

14. The polypeptide according to claim 4, wherein said receptor is in a tissue preparation derived from a mammal.

15. The polypeptide according to claim 5, wherein said receptor is in a tissue preparation derived from a mammal.

16. The polypeptide according to claim 6, wherein said receptor is in a tissue preparation derived from a mammal.

17. The polypeptide according to claim 7, wherein said receptor is in a tissue preparation derived from a mammal.

18. The polypeptide according to claim 8, wherein said receptor is in a tissue preparation derived from a mammal.

19. The polypeptide according to claim 9, wherein said receptor is in a tissue preparation derived from a mammal.

20. The polypeptide according to claim 10, wherein said receptor is in a tissue preparation derived from a mammal.

* * * * *

UNITED STATES PATENT AND TRADEMARK OFFICE
CERTIFICATE OF CORRECTION

| | | |
|---|---|---|
| PATENT NO. | : 6,462,016 B1 | Page 1 of 1 |
| APPLICATION NO. | : 08/969744 | |
| DATED | : October 8, 2002 | |
| INVENTOR(S) | : Kawori Wakita et al. | |

It is certified that error appears in the above-identified patent and that said Letters Patent is hereby corrected as shown below:

Column 1, immediately after the title of the invention, please insert:
--This invention was made with Government support under Grant No. AR042005 awarded by the National Institutes of Health. The Government has certain rights in this invention.--

Signed and Sealed this

Eighth Day of April, 2008

JON W. DUDAS
*Director of the United States Patent and Trademark Office*